(12) United States Patent
Klee

(10) Patent No.: US 11,455,441 B1
(45) Date of Patent: *Sep. 27, 2022

(54) COMPUTER-BASED COMPUTATIONAL TOOLS FOR USE IN ELECTROPHYSIOLOGY

(71) Applicant: Maurice M. Klee, Fairfield, CT (US)

(72) Inventor: Maurice M. Klee, Fairfield, CT (US)

( * ) Notice: Subject to any disclaimer, the term of this patent is extended or adjusted under 35 U.S.C. 154(b) by 580 days.

This patent is subject to a terminal disclaimer.

(21) Appl. No.: 16/517,778

(22) Filed: Jul. 22, 2019

Related U.S. Application Data

(63) Continuation of application No. 14/257,069, filed on Apr. 21, 2014, now Pat. No. 10,402,507, which is a continuation of application No. 13/467,615, filed on May 9, 2012, now Pat. No. 8,706,466, which is a continuation of application No. 12/403,389, filed on Mar. 13, 2009, now Pat. No. 8,180,617.

(60) Provisional application No. 61/088,676, filed on Aug. 13, 2008, provisional application No. 61/036,100, filed on Mar. 13, 2008.

(51) Int. Cl.
*G01N 31/00* (2006.01)
*G06F 30/20* (2020.01)
*G01N 27/00* (2006.01)

(52) U.S. Cl.
CPC ............ *G06F 30/20* (2020.01); *G01N 27/00* (2013.01)

(58) Field of Classification Search
None
See application file for complete search history.

(56) References Cited

PUBLICATIONS

Nordlund, Kai. "Molecular dynamics simulation of ion ranges in the 1-100 keV energy range." Computational materials science 3.4 (1995): 448-456.*
Heermann, Dieter W. "Computer-simulation methods." Computer Simulation Methods in Theoretical Physics. Springer, Berlin, Heidelberg, 1990. 8-12.*
Sachs, Jonathan N., Paul S. Crozier, and Thomas B. Woolf. "Atomistic simulations of biologically realistic transmembrane potential gradients." The Journal of chemical physics 121.22 (2004): 10847-10851.*
Klee, Maurice M. "Charge distributions that cause current to enter a pore in a biological membrane." 2007 29th Annual International Conference of the IEEE Engineering in Medicine and Biology Society. IEEE, 2007.*

* cited by examiner

*Primary Examiner* — Anna Skibinsky

(57) ABSTRACT

Computer-based computational tools for use in determining spatial charge distributions for biological systems that include one or more biological membranes are provided. At least one of the biological membrane includes at least two regions having different electrical properties, e.g., the biological membrane can include a pore having a higher conductivity than the surrounding bulk membrane. In other cases, the membrane can include non-active and active regions, with conservative fields acting at the non-active regions and a combination of conservative and non-conservative fields acting at the active regions. The non-conservative fields can, for example, originate from differences in ionic concentrations of the type which generate Nernst potential differences across membranes. Using the computer-based computational tools, charge distributions not previously known to exist have been discovered, e.g., ring-shaped charge distributions in the vicinity of an active pore.

20 Claims, 21 Drawing Sheets

Using the calculation start condition established during problem setup (FIG. 1A), set the charge distribution at time = t equal to the starting charge distribution.

Using the system geometry and symmetry established during problem setup (FIG. 1A), define the portion of the system over which iterations are to be performed.

Progress through the calculation cells of the defined portion of the system calculating values for the charge distribution at time = t + Δt based on values for the charge distribution at time = t using the electrical parameters established during problem setup (FIG. 1A) and such of Equations (1) through (7) as appropriate to the calculation cell being iterated.

Output criterion satisfied? — Y → Output final or intermediate results.

N

Termination criterion satisfied? — N → Replace charge distribution at time = t with charge distribution calculated for time = t + Δt.

Y

End

FIG. 1B

COMPUTER-BASED COMPUTATIONAL TOOLS FOR USE IN ELECTROPHYSIOLOGY

This application is a continuation of U.S. application Ser. No. 14/257,069 filed Apr. 21, 2014, which is a continuation of U.S. application Ser. No. 13/467,615 filed May 9, 2012, now U.S. Pat. No. 8,706,466, which is a continuation of U.S. application Ser. No. 12/403,389 filed Mar. 13, 2009, now U.S. Pat. No. 8,180,617, the contents of which in their entireties are hereby incorporated by reference.

This application also claims the benefit under 35 USC § 119(e) of U.S. Provisional Application No. 61/036,100 filed Mar. 13, 2008, and U.S. Provisional Application No. 61/088,676 filed Aug. 13, 2008, the contents of each of which is hereby incorporated herein by reference in its entirety.

The text and drawings of the disclosure of this patent document contain material which is subject to copyright protection. The copyright owner has no objection to the facsimile reproduction by anyone of the patent document or the patent disclosure, as it appears in the Patent and Trademark Office patent file or records, but reserves all other copyright rights whatsoever.

I. FIELD OF THE INVENTION

This invention relates to electrophysiology and, in particular, to computer-based computational tools for analyzing and interpreting electrophysiological data, designing electrophysiological experiments, and discovering heretofore unknown mechanisms and phenomena of electrophysiological systems.

II. BACKGROUND OF THE INVENTION

Computational tools have been used in interpreting electrophysiological data and in discovering electrophysiological phenomena for well more than a century. One of the earliest uses of a computational tool in electrophysiology was the application of Lord Kelvin's mathematical model for the propagation of electrical signals through undersea telegraph cables (cable theory) to the problem of conduction of action potentials along nerve and muscle fibers. See Hermann (1905).

Over the years, cable theory has been extended to structures much more complex than simple fibers, so that today it is used in the study of such diverse physiological phenomena as the electrical potentials produced by populations of neurons, the role of dendritic spines in information processing, and the generation of action potentials from synaptic input on branched dendritic trees. See Koch and Segev (1998). Indeed, a number of professional computer programs are now available which allow experimental researchers to use cable theory and, for example, the Hodgkin-Huxley equations to analyze complex experimental data. See, for example, the NEURON software program available at Yale University and Duke University, which is documented in Carnevale and Hines (2005). See also the neural modeling project, nicknamed the Blue Brain Project, being conducted by IBM and The Ecole Polytechnique Fédérale de Lausanne.

At a phenomenological level substantially below that of cable theory, other computational tools have been developed based on the Poisson-Boltzmann and the Poisson-Nernst-Planck equations. These tools have been applied to problems involving the movement of ions in and around biological membranes. Molecular dynamics analyses directed to the movement of individual ions through pores have also been proposed. See Allen et al. (2001). Recently, the mechanisms underlying the gating of biological pores (channels) has been studied using these types of tools. See Islas and Sigworth (2001).

At a phenomenological level substantially above that of cable theory, computational tools based on volume conductor analyses have been used to calculate in detail the electrical fields surrounding individual nerve fibers as well as those produced by entire organs, such as the heart or brain. For example, extensive engineering efforts have been applied to what has become known as the "reverse problem," where the goal is to determine electrical sources from measurements, e.g., EEG or EKG measurements, made on a patient's skin.

A common characteristic of the computational tools used to date has been their focus on electrical potentials. In addition to the foregoing, see, for example, U.S. Pat. Nos. 5,355,435, 5,947,899, and 7,174,325. This, of course, is the natural parameter to calculate since in practice what researchers measure are electrical potential differences. However, electrical potentials are not primary variables but are the result of "unseen" charge distributions.

As illustrated by the examples set forth below, using the computer-based computational tools of the present invention, it has been found that the charge distributions associated with biological membranes having regions with different electrical properties (e.g., regions with different conductivities and/or regions with and without non-conservative fields (e.g., fields due to chemical potentials)) are highly complex. The complexity is seen in both the charge distributions' temporal and spatial behavior.

The charge distributions identified by the computer-based computational tools of the invention can be expected to play significant roles in the functioning of biological membranes and systems. As just one example, ligand-gated pores change state in response to the presence of the ligand (typically charged) in the vicinity of the pore.

Using the computer-based computational tools of the present invention, spatial and temporal distributions for charged ligands in the vicinity of a pore can be calculated. By studying these distributions, better understandings can be achieved of the operation of such pores. Voltage-gated pores, as well as electrical synapses, can be similarly studied. In short, wherever charged species play a role in the operation of biological membranes, the computer-based computational tools of the present invention can be used to provide insight into how those species are distributed in space, in time, or in both space and time.

In recent years, the relationship between surface charge distributions and the currents they generate has been the subject of original research in the field of physics education and has served as a central theme of at least some textbooks. See Chabay and Sherwood (2002); Heald (1984); Jackson (1996); Jefimenko (1989); Preyer (2000); and Preyer (2002). Indeed, for more than 25 years, it has been known that local surface charge accumulations are needed for current to turn a corner. See Rosser (1970). Yet, as noted above, in the field of electrophysiology, the focus has been on electrical potentials, not charge distributions. As a consequence many fundamental phenomena have been poorly understood or not understood at all. The present invention is directed to providing computer-based computational tools for addressing this deficit in the existing state of the art.

III. SUMMARY OF THE INVENTION

In accordance with a first aspect, the invention provides a computer-based method for computing a spatial distribution, a time series, or a spatial distribution and a time series of at least one electrical variable (e.g., an electrical potential difference, an electric field, a current density, a total current, a surface charge density, a total quantity of charge, a capacitance value, a resistance value, a time constant, etc.) of an electrophysiological system that comprises a biological membrane (9) comprising: an intracellular side,
(ii) an extracellular side, and
(iii) at least two membrane regions (11, 13, 19) with different electrical properties (e.g., different conductivities and/or the presence/absence of non-conservative fields),
said method comprising using a computer to determine a spatial charge distribution for at least a portion of the system using a $1/r^2$ law to express at least some of the system's electrical fields, where the r's represent distances to quantities of charge, said spatial charge distribution being determined without first determining an electrical potential distribution and then differentiating that potential distribution to determine the charge distribution.

In accordance with a second aspect, the invention provides a computer-based method for computing a spatial charge distribution for at least a portion of an electrophysiological system that comprises a biological membrane (9), said method comprising using a computer to:
(a) represent at least a portion of the system by a plurality of cubic calculation cells; and
(b) calculate a quantity of charge entering/leaving at least one calculation cell using an equation of the form:

$$\Delta q = -\sigma(E_n + E'n)s^2 \Delta t;$$

where $\Delta q$ is the quantity of charge entering into a face of the calculation cell during a time step $\Delta t$, s is the length of an edge of the face, $\sigma$ is the smaller of the conductivities on the inside and outside of the face, and $E_n$ and $E'_n$ are fields acting in the direction of the face's outward normal, $E_n$ being the net outward normal electric field at the center of the face produced by the spatial charge distribution at the beginning of the time step, and $E'_n$ being a non-conservative field which acts at the face.

In accordance with a third aspect, the invention provides a computer-based method for computing a spatial charge distribution for at least a portion of an electrophysiological system that comprises a biological membrane (9) having an intracellular side and an extracellular side, said method comprising using a computer to:
(a) represent said portion of the system by a plurality of cubic calculation cells, each calculation cell having six faces and edges of length s;
(b) represent a non-conservative field $E'_n$ at a face of at least one calculation cell by an equation of the form:

$$E'_n = -V_{Nernst}/s,$$

said face having an outward normal that points from the intracellular side of the face towards the extracellular side of the face; and
(c) represent a non-conservative field $E'_n$ at a face of at least one calculation cell by an equation of the form:

$$E'_n = +V_{Nernst}/s$$

said face having an outward normal that points from the extracellular side of the face towards the intracellular side of the face;
where $V_{Nernst}$ is a Nernst potential between the intracellular and extracellular sides of the membrane.

In accordance with a fourth aspect, the invention provides a computer-based method for computing a spatial charge distribution for a portion of an electrophysiological system that comprises a biological membrane (9) comprising:
(i) an inner region (11),
(ii) a perimeter region (19) which contacts at least a portion of the outer perimeter of the inner region (11), and
(iii) an outer region located outboard of the perimeter region,
said method comprising using an electrical property of at least a portion of the perimeter region (19) to represent at least a portion of the outer region and thereby avoid the need to explicitly calculate a spatial charge distribution for said at least a portion of the outer region.

In accordance with a fifth aspect, the invention provides a computer-based method for computing a spatial charge distribution for at least a portion of an electrophysiological system that comprises a biological membrane (9), said method comprising using a computer to:
(a) represent at least a portion of the system by a plurality of cubic calculation cells; and
(b) calculate a quantity of charge entering/leaving at least one calculation cell using an equation having a form selected from the group consisting of:

$$\Delta q = -E_n s^3 \Delta t / R_m \text{ and } \Delta q = -(E_n + E'_n)s^3 \Delta t / R_m;$$

where $\Delta q$ is the quantity of charge entering into a face of the calculation cell during a time step $\Delta t$, s is the length of an edge of the face, $R_m$ is the specific resistance of a portion of the biological membrane located at the face, and $E_n$ and $E'_n$ are fields acting in the direction of the face's outward normal, $E_n$ being the net outward normal electric field at the center of the face produced by the spatial charge distribution at the beginning of the time step, and $E'_n$ being a non-conservative field which acts at the face.

In accordance with a sixth aspect, the invention provides a computer-based method for computing a spatial charge distribution associated with a biological membrane (9) comprising using a computer to:
(a) represent the membrane (9) as being located between two volumes (15, 17) of conductive media each volume being bounded by non-conductive walls except for the portion of the volume bounded by the membrane; and
(b) determine a spatial charge distribution on at least a portion of the surface of the membrane using a $1/r^2$ law to express electrical fields, where the r's represent distances to quantities of charge.

In accordance with a seventh aspect, the invention provides a computer-based method for computing a spatial charge distribution for at least a portion of an electrophysiological system that comprises a biological membrane (9) having an intracellular side and an extracellular side, said method comprising:
(I) inputting data to a computer regarding (i) the structure and dimensions of the portion of the electrophysiological system, (ii) at least one electrical property of the portion of the electrophysiological system, and (iii) the value $V_{Nernst}$ of at least one Nernst potential between the intracellular and extracellular sides of the biological membrane;
(II) using the computer to:
(a) represent said portion of the electrophysiological system by a plurality of cubic calculation cells, each calculation cell having six faces and edges of length s;
(b) represent a non-conservative field $E'_n$ at a face of at least one calculation cell by an equation of the form:

$$E'n = -V_{Nernst}/s,$$

said face having an outward normal that points from the intracellular side of the face towards the extracellular side of the face;

(c) represent a non-conservative field $E'_n$ at a face of at least one calculation cell by an equation of the form:

$$E'_n = +V_{Nernst}/s$$

said face having an outward normal that points from the extracellular side of the face towards the intracellular side of the face; and (d) determine the spatial charge distribution for said portion of the electrophysiological system using (i) the plurality of cubic calculation cells, (ii) the representations of the non-conservative field, and (iii) a $1/r^2$ law to express at least some of the electrophysiological system's electrical fields, where the r's represent distances to quantities of charge, said spatial charge distribution being determined without first determining an electrical potential distribution and then differentiating that potential distribution to determine the charge distribution; and (III) displaying at least a part of the spatial charge distribution for said portion of the electrophysiological system determined in step (II)(d) (see, for example, FIG. 12A).

The reference numbers and figure number used in the above summaries of the various aspects of the invention are only for the convenience of the reader and are not intended to and should not be interpreted as limiting the scope of the invention. More generally, it is to be understood that both the foregoing general description and the following detailed description are merely exemplary of the invention and are intended to provide an overview or framework for understanding the nature and character of the invention.

Additional features and advantages of the invention are set forth in the detailed description which follows, and in part will be readily apparent to those skilled in the art from that description or recognized by practicing the invention as described herein. The accompanying drawings are included to provide a further understanding of the invention, and are incorporated in and constitute a part of this specification. It is to be understood that the various features of the invention disclosed in this specification and in the drawings can be used in any and all combinations.

IV. BRIEF DESCRIPTION OF THE DRAWINGS

FIG. 1 is a representative flow chart of an embodiment of the invention. FIG. 1 is a two-part figure having an A part and a B part. FIG. 1A shows the setup portion of the process and FIG. 1B shows the iteration and output portions.

FIG. 2 is a schematic diagram illustrating a patch of membrane for which charge distributions can be calculated in accordance with an embodiment of the invention. FIG. 2 is a two-part figure having an A part and a B part. FIG. 2A is a top view of the patch and FIG. 2B is a cross-sectional view for a midplane orthogonal to the membrane.

FIG. 3 is a schematic diagram illustrating a patch of membrane for which charge distributions can be calculated in accordance with an embodiment of the invention. FIG. 3 is a two-part figure having an A part and a B part. FIG. 3A is a top view of the patch and FIG. 3B is a cross-sectional view for a midplane orthogonal to the membrane. This embodiment uses faces of calculation cells to represent the membrane. It also includes a perimeter path through the membrane patch and a source and sink of applied current.

FIG. 4 shows the geometry and dimensions of the system analyzed in Example 1. The plot of this figure and of FIG. 5 are for a midplane of the system orthogonal to the membrane.

FIG. 5 shows charge distributions calculated using an embodiment of the invention. The figure shows the charge distribution before (upper panel) and after (lower panel) the opening of a pore. The opened pore has current-turning charges at its entrance and exit ends, which have a sign opposite to that of the charge on the surrounding membrane and aid in moving current into and out of the pore.

Figure 4:
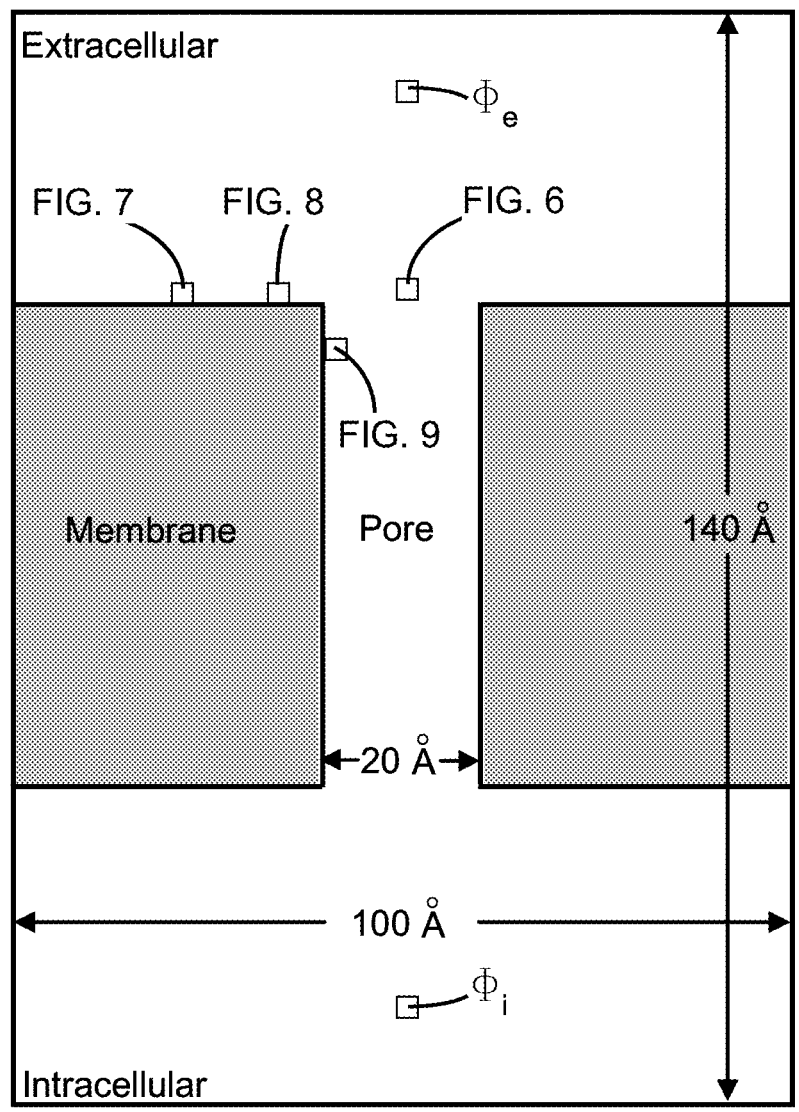
Figure 8:
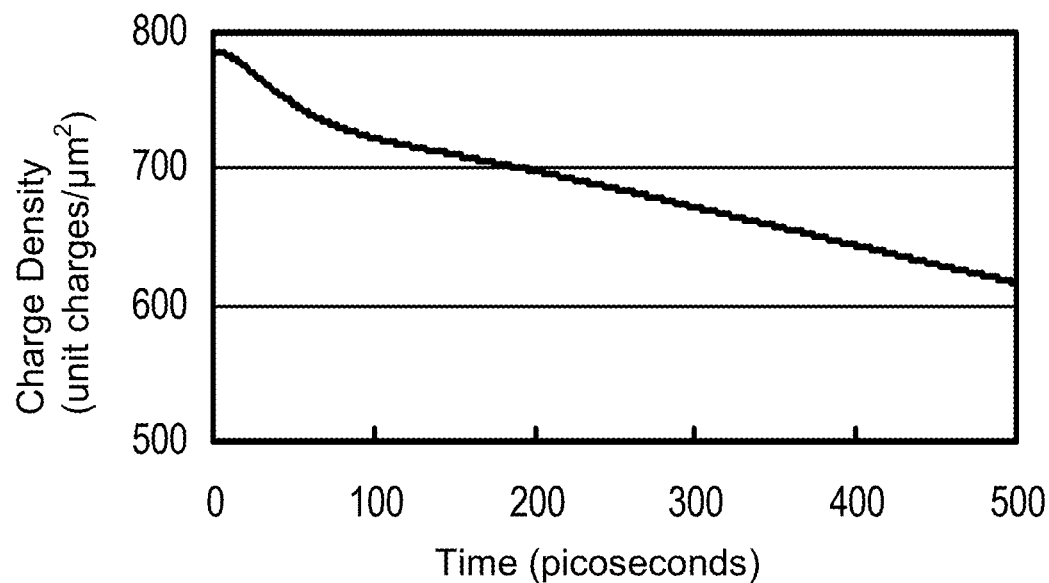

FIG. 8 shows the time course of charge decay at the "FIG. 8" point of FIG. 4. The decay has an initial portion (0 to ~100 picoseconds) with a time constant τ of 1,065 picoseconds. Thereafter, the charge decays in accordance with the slower RC time constant of the overall system (τ=2,500 picoseconds).

Figure 9:
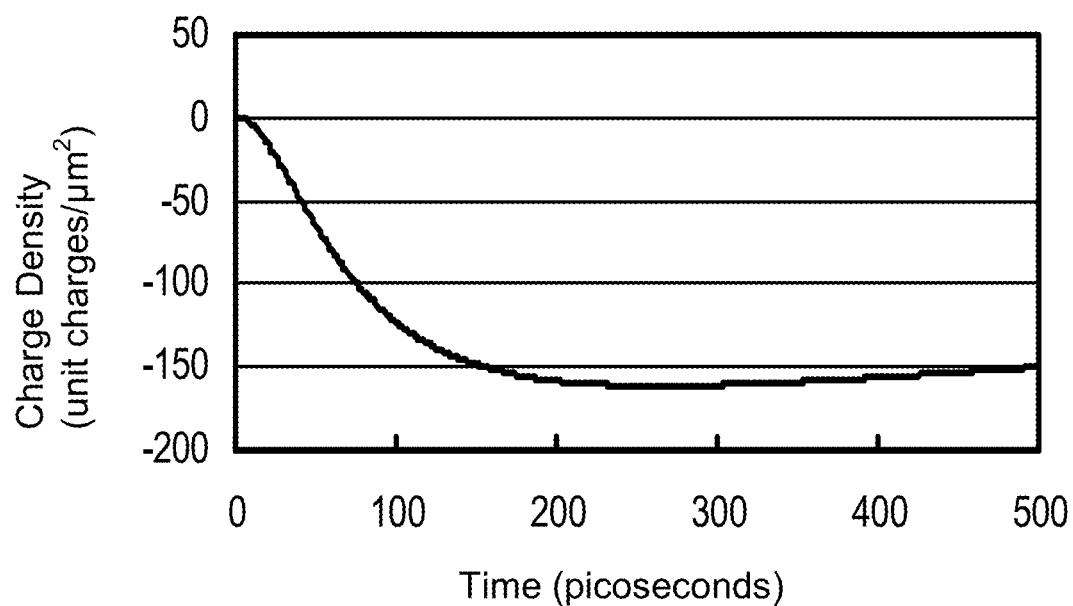

FIG. 9 shows the time course of the surface charge density at the "FIG. 9" point of FIG. 4. Rather than decaying, the charge (current-turning charge) at this point initially grows in magnitude for about 200 picoseconds, levels off, and only then decays in accordance with the RC time constant of the overall system.

Figure 10:
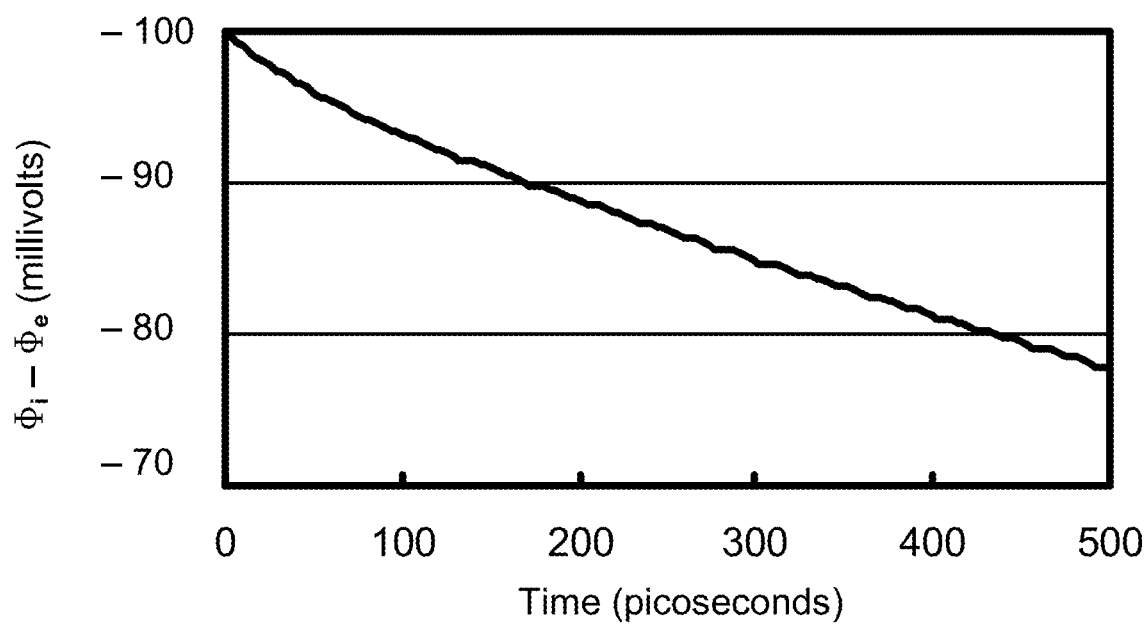

FIG. 10 shows the time course of decay of the transmembrane potential measured between the $\Phi_i$ and $\Phi_e$ points of FIG. 4. The time constant τ for the decay is 2,114 picoseconds which corresponds to the RC time constant of the overall system.

Figure 11A:
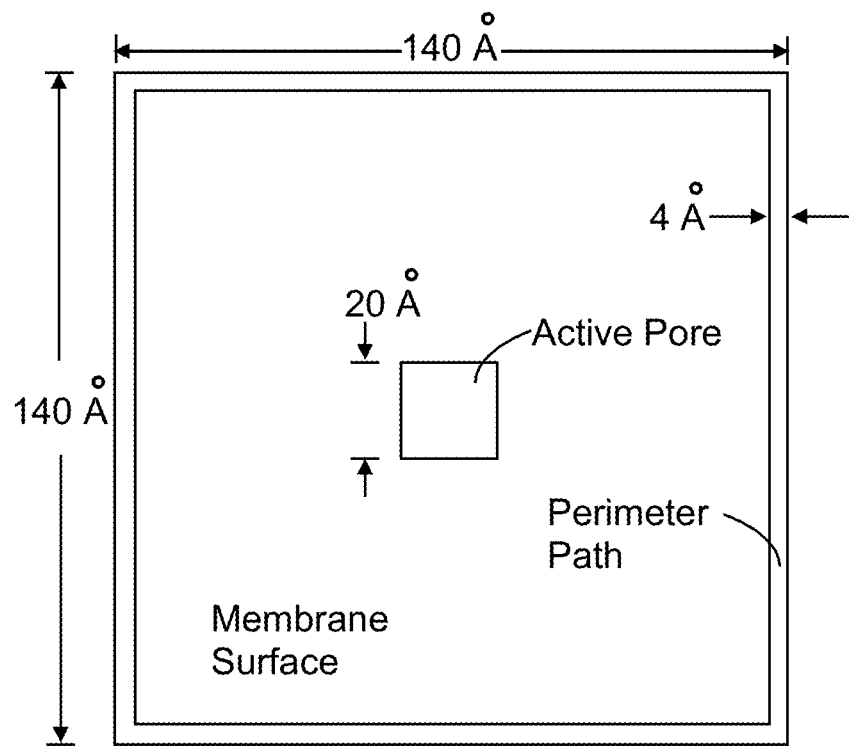
Figure 11B:
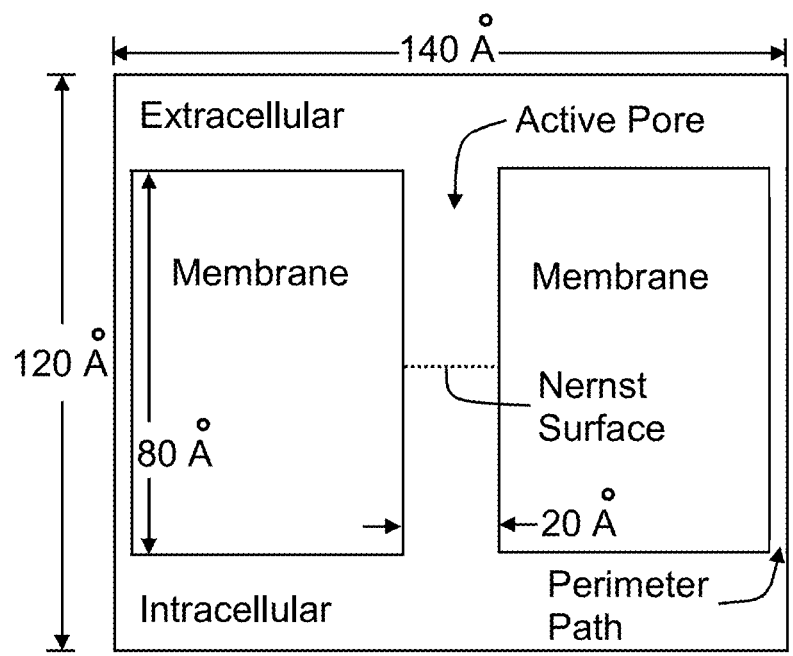

FIG. 11 shows the geometry and dimensions of the system analyzed in Example 2. The system has an active pore at the center of a patch of membrane and a path (perimeter path) through the membrane around the entire perimeter of the patch. FIG. 11 is a two-part figure having an A part and a B part. FIG. 11A is a top view of the patch and FIG. 11B is a cross-sectional view for a midplane orthogonal to the membrane.

Figure 12A:
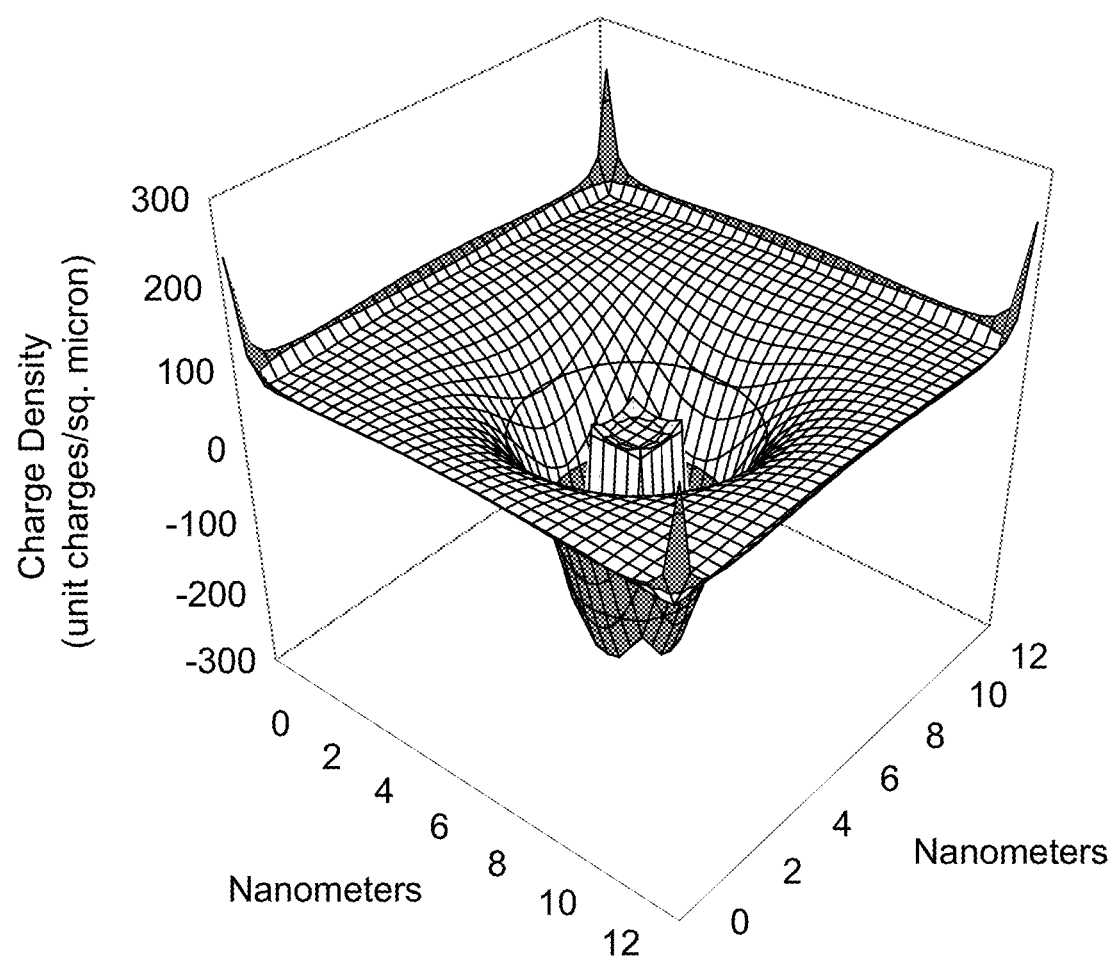
Figure 12B:
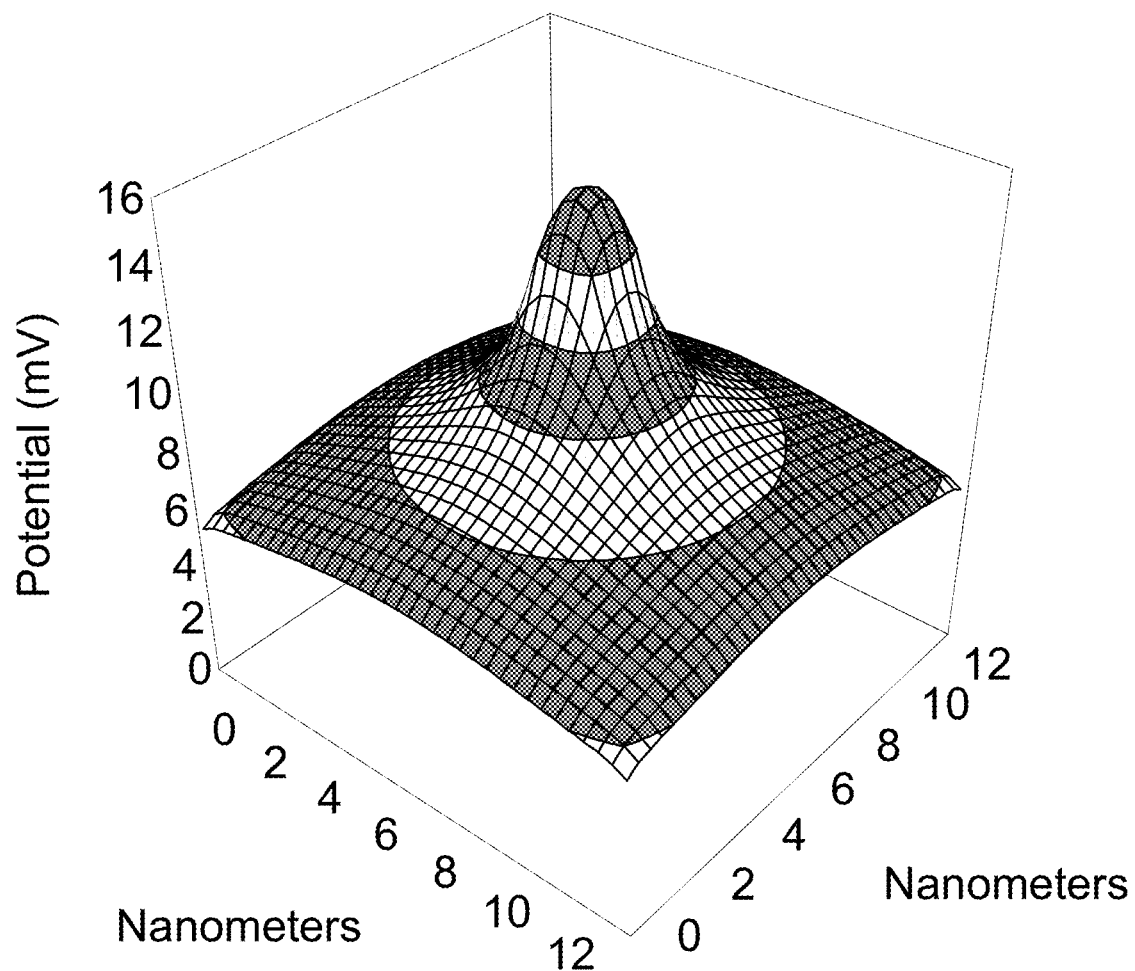

FIGS. 12A and 12B are topographic plots of surface charge density (FIG. 12A) and potential (FIG. 12B) on the extracellular surface of the membrane patch of FIG. 11.

Figure 13A:
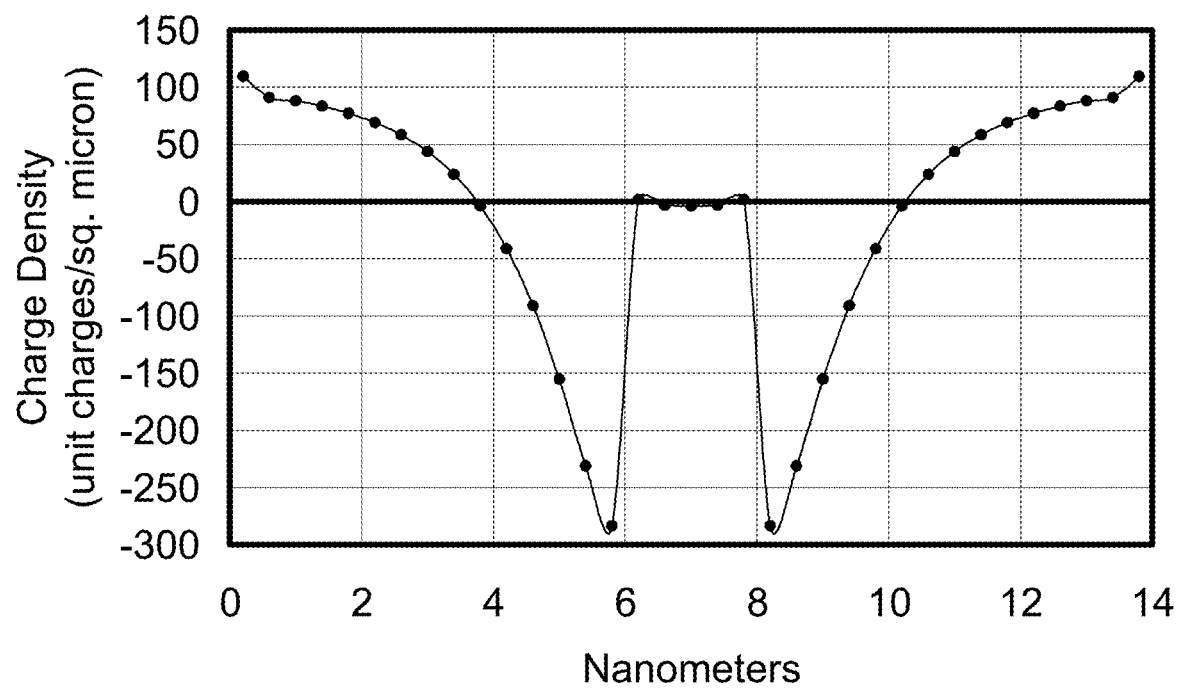
Figure 13B:
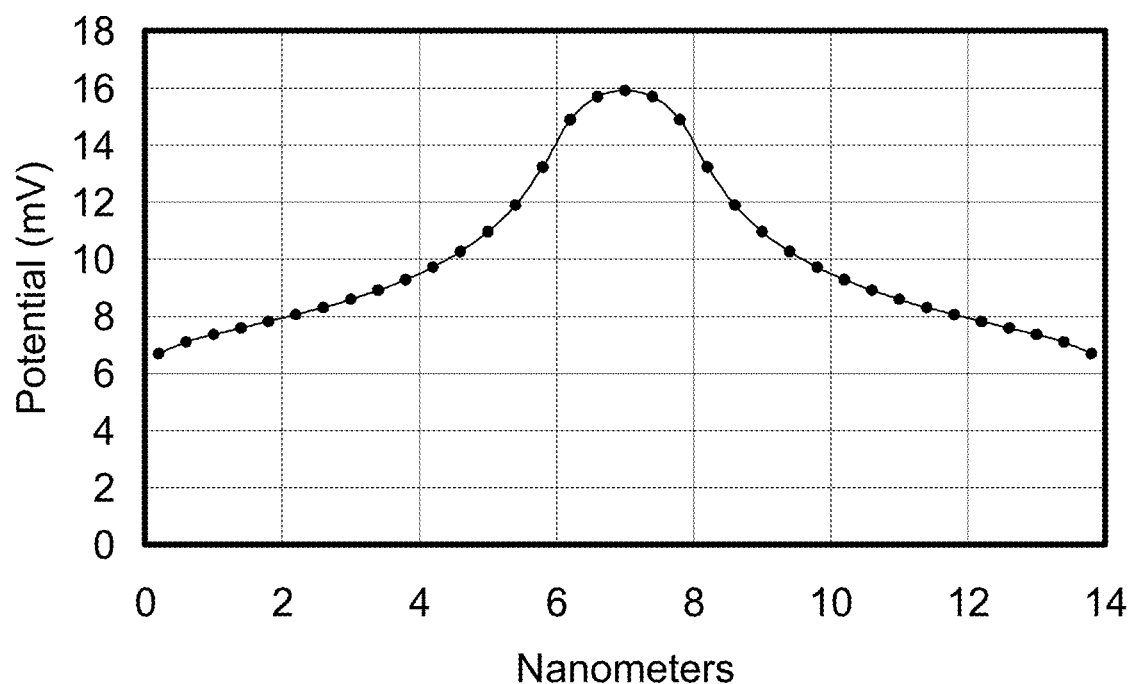

FIGS. 13A and 13B are plots of surface charge density (FIG. 13A) and potential (FIG. 13B) on the extracellular surface of the membrane patch of FIG. 11 along a midplane line on that surface.

Figure 14:
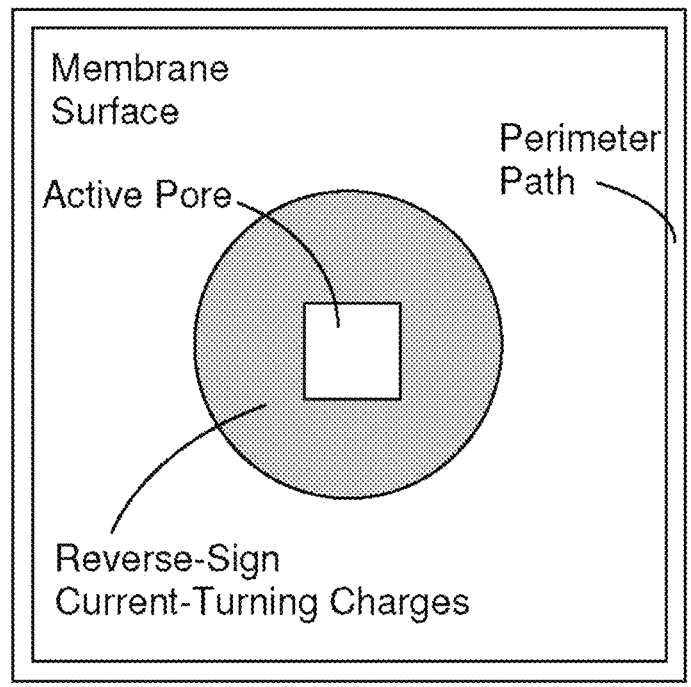

FIG. 14 shows the location of the reverse-sign, current-turning charges on the extracellular surface of the membrane patch of FIG. 11.

Figure 15:
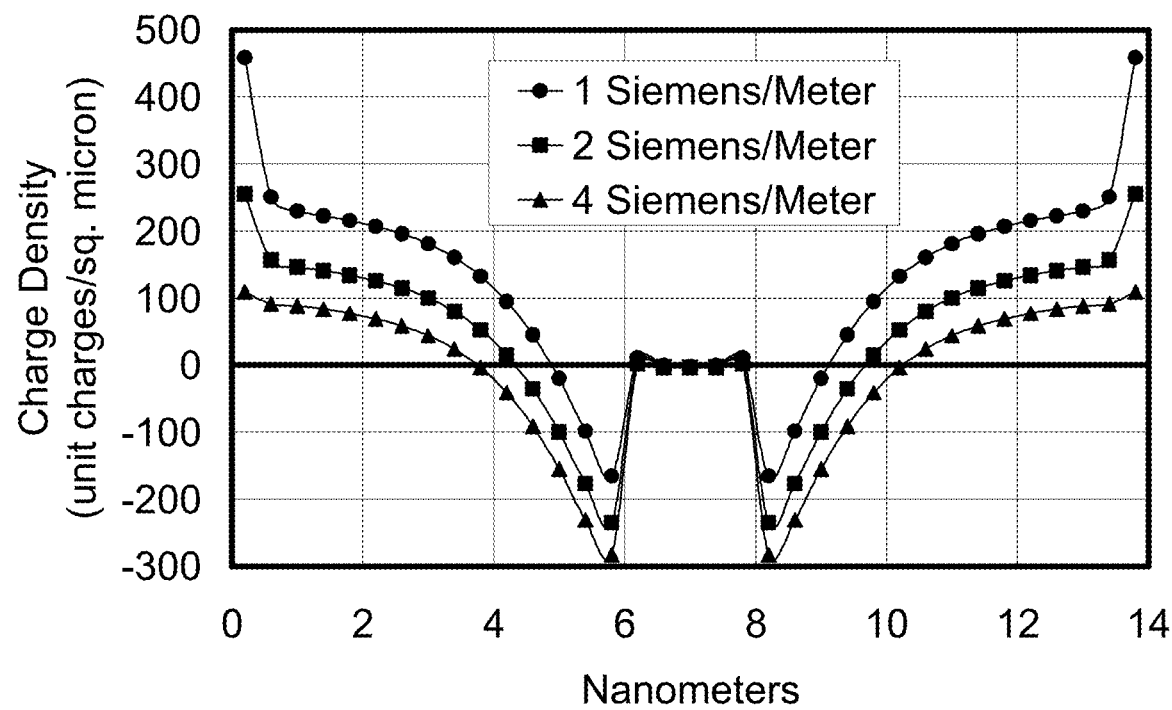

FIG. 15 is a plot of surface charge density on the extracellular surface of the membrane patch of FIG. 11 along a midplane line on that surface for different conductivities of the perimeter path through the membrane.

Figure 16:
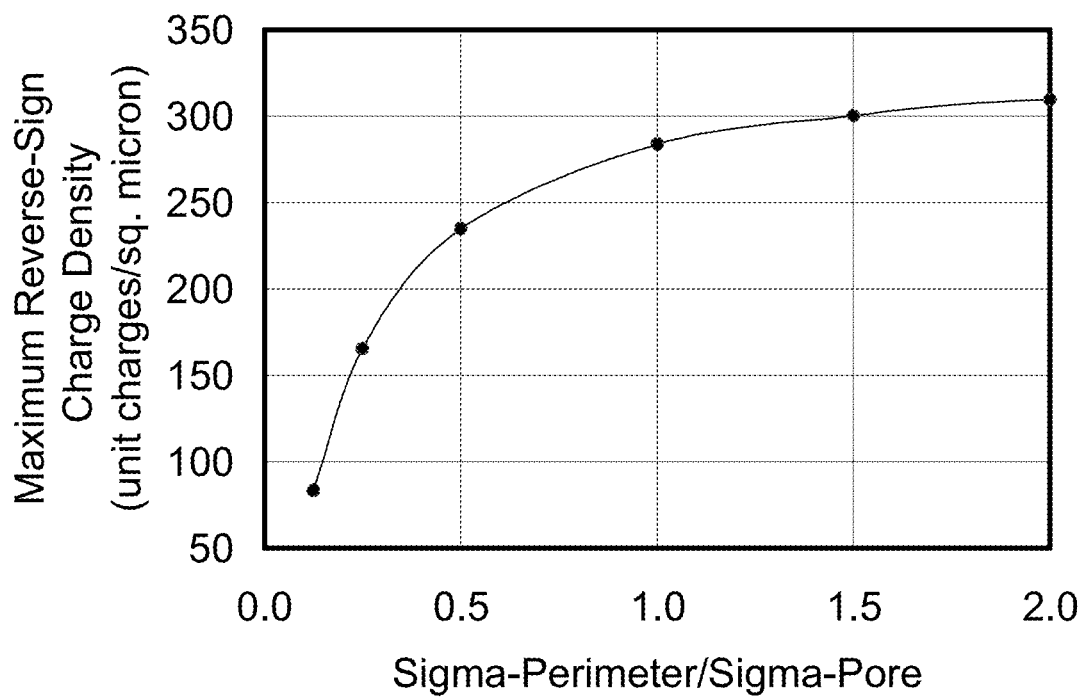

FIG. 16 is a plot of the magnitude of the maximum reverse-sign surface charge density in the vicinity of the active pore as a function of the ratio of the conductivity of the perimeter path through the membrane (sigma-perimeter) to the pore conductivity (sigma-pore).

Figure 17A:
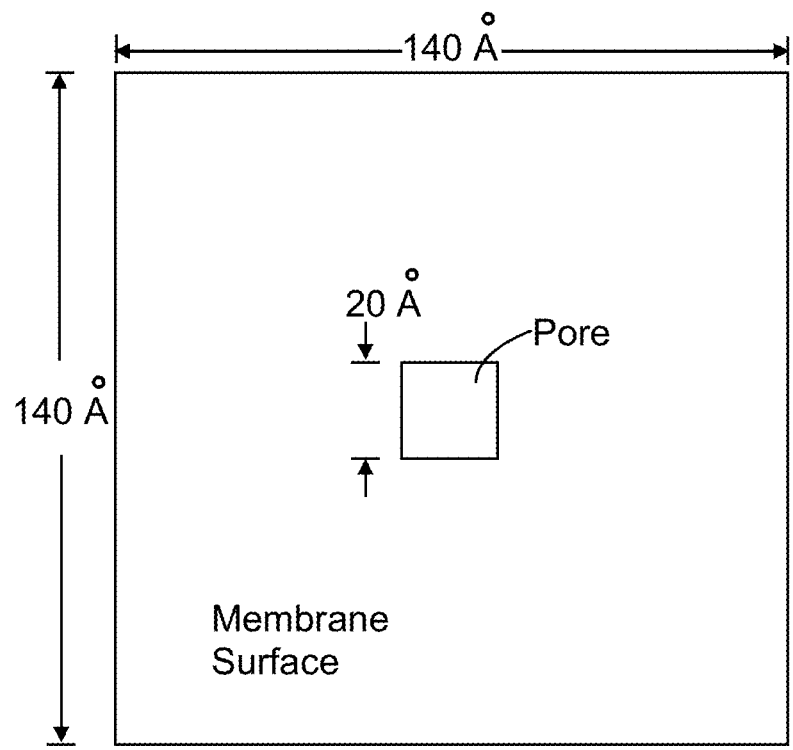
Figure 17B:
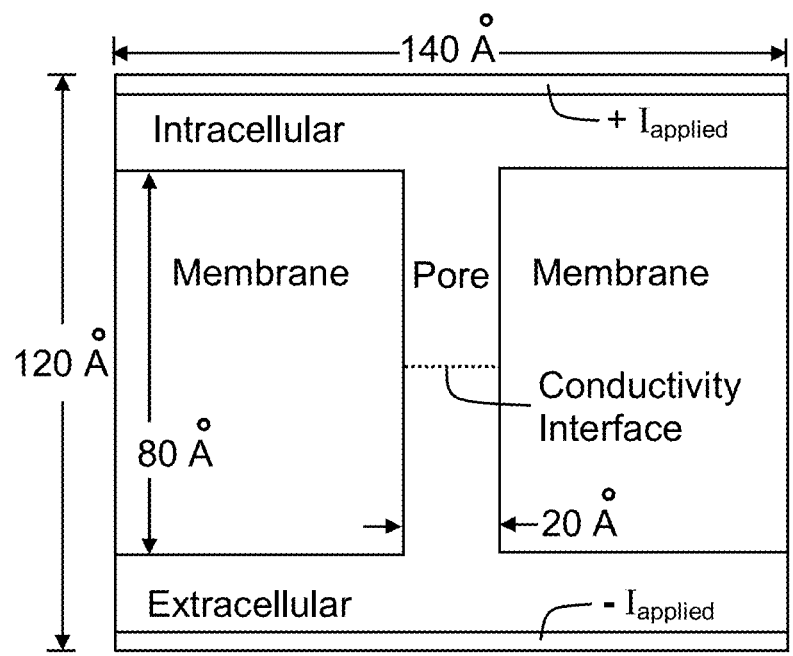

FIG. 17 shows the geometry and dimensions of the system analyzed in Example 3. The system has a passive pore at the center of a patch of membrane, a source ($+I_{applied}$) and a sink ($-I_{applied}$) for applied current, and extracellular and intracellular conductivities which can be the same or different. The extracellular and intracellular media meet at the center of the pore as shown by the dashed line (conductivity interface) in this figure. FIG. 17 is a two-part figure having an A part and a B part. FIG. 17A is a top view of the patch and FIG. 17B is a cross-sectional view for a midplane orthogonal to the membrane.

Figure 18:
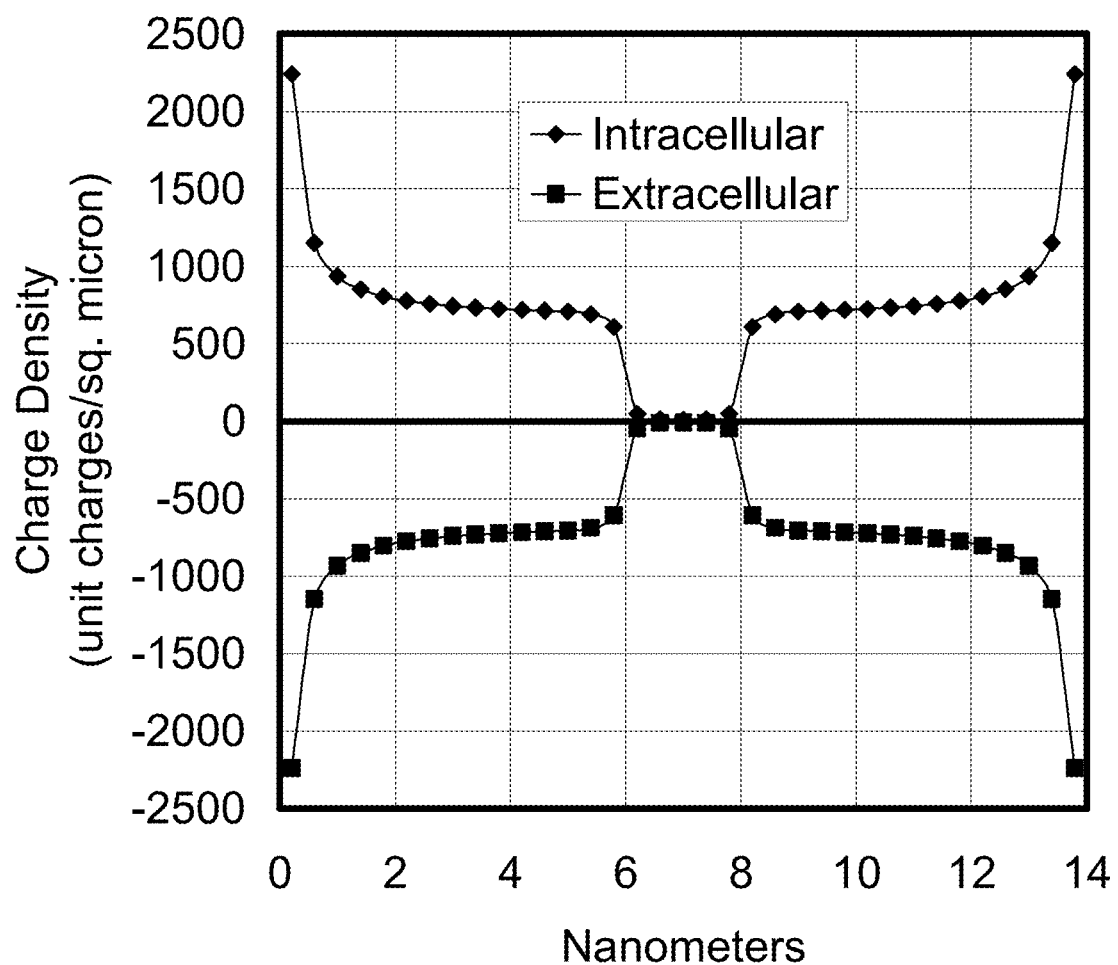

FIG. 18 is a plot of surface charge densities on the extracellular and intracellular surfaces of the membrane patch of FIG. 17 along midplane lines on those surfaces for equal intracellular and extracellular conductivities of 0.727 siemens/meter ($\rho$=137.5 ohm-cm).

Figure 19:
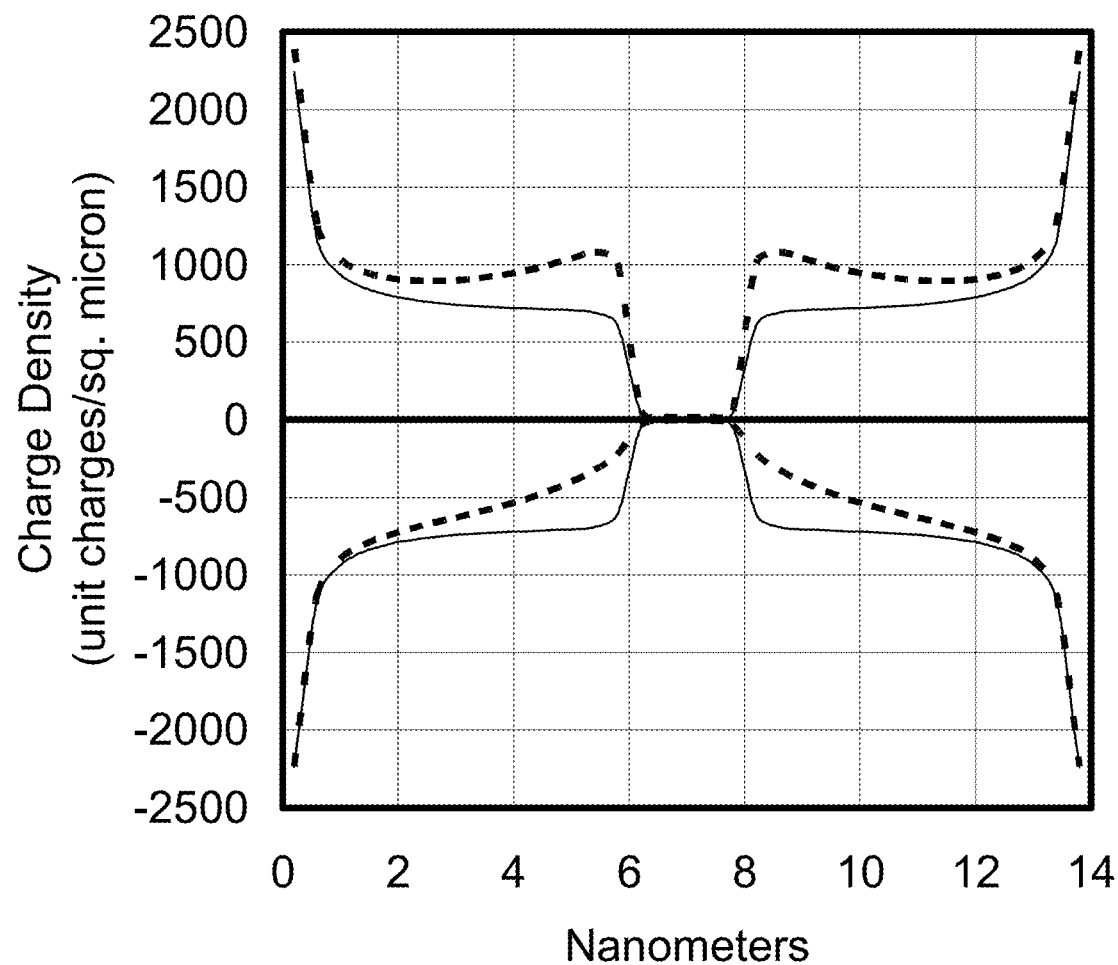

FIG. 19 is a plot of surface charge densities on the extracellular and intracellular surfaces of the membrane patch of FIG. 17 along midplane lines on those surfaces. The solid curves are for the case of equal intracellular and extracellular conductivities of 0.727 siemens/meter ($\rho$=137.5 ohm-cm), and the dashed curves are for an intracellular conductivity of 0.4 siemens/meter ($\rho$=250 ohm-cm) and an extracellular conductivity of 4.0 siemens/meter ($\rho$=25 ohm-cm).

Figure 20:
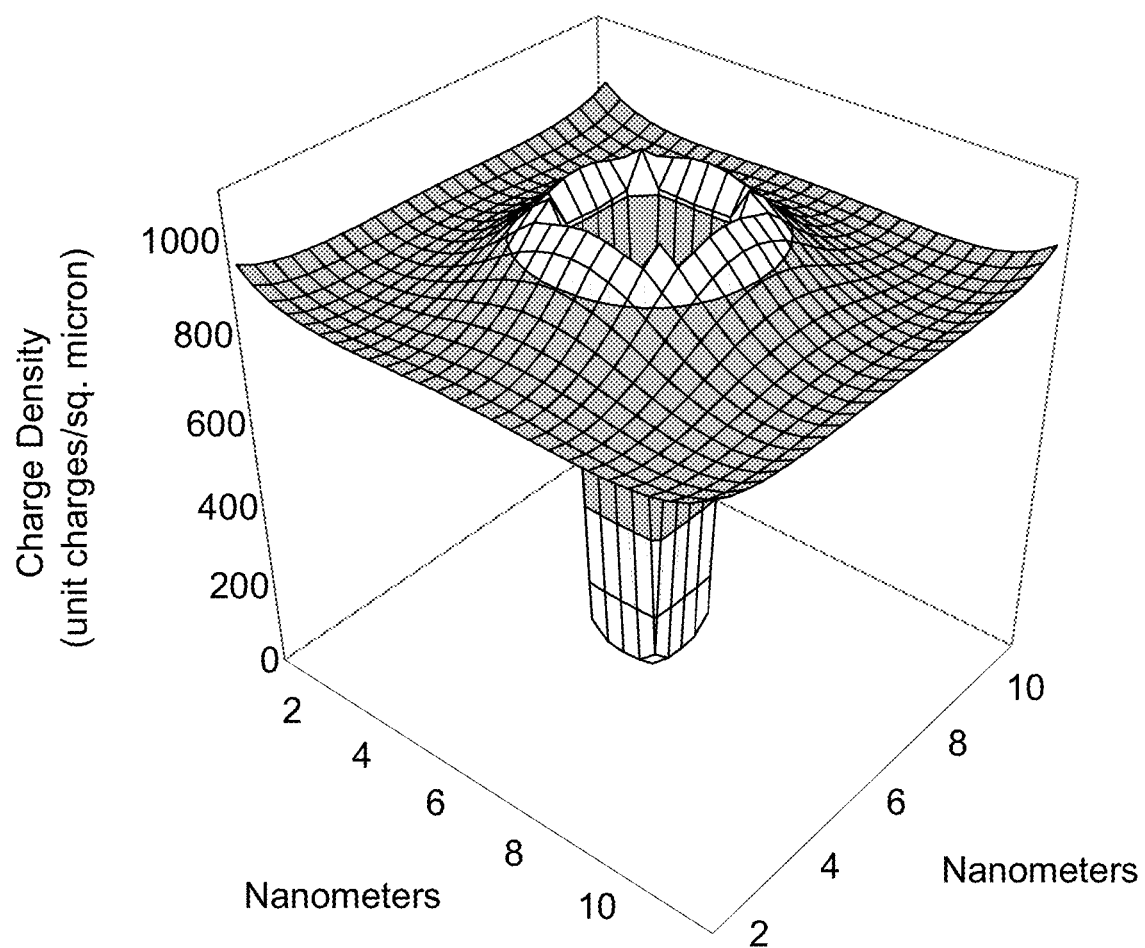

FIG. 20 is a topographic plot of surface charge density on the intracellular surface of the membrane patch of FIG. 17 for an intracellular conductivity of 0.4 siemens/meter ($\rho$=250 ohm-cm) and an extracellular conductivity of 4.0 siemens/meter ($\rho$=25 ohm-cm). The spatial extent of the plot has been truncated to remove the edge effect and thereby make the ring effect easier to see.

V. DETAILED DESCRIPTION OF THE INVENTION AND ITS PREFERRED EMBODIMENTS

A. Calculation of Charge Distributions

As discussed above, in accordance with an aspect of the present invention, a spatial charge distribution for at least a portion of a biological system is calculated using a $1/r^2$ law to express at least some of the system's fields. Optionally, a time series of spatial charge distributions are calculated for said portion.

In one embodiment, the portion of the biological system to be analyzed is divided into an array of three dimensional calculation cells. Cubic calculation cells are generally preferred because they simplify the description of the geometry being analyzed, and also simplify the calculation process and its programming. However, calculation cells having other shapes can be used if desired.

Each calculation cell is assigned a conductivity (or, equivalently, a resistivity), which may be zero for calculation cells located in an insulator (e.g., calculation cells in the wall of a glass or plastic container, the wall of a microelectrode, or in bulk membrane (see Section V(B) below)). Each calculation cell is also assigned an initial quantity of charge, which may be based on, for example, a prior calculation, an educated guess for a state of the system (e.g., a steady state or quasi-steady state charge distribution for the system), or some other consideration, e.g., ease of programming as, for example, an initial charge distribution that is uniform over all or a part of the system. The initial quantity of charge can be and often is zero for many or all of the calculation cells.

The charge distributions, including the initial charge distributions, can be expressed in various units. For biological systems, it has been found convenient to use SI units to perform calculations and to report results in terms of surface charge densities in units of elementary charges per square micron, although other units for the calculations and the reporting of results can, of course, be used if desired. Often, the quantity of charge in a calculation cell will be less than one elementary charge. Such values can be interpreted in terms of temporal probabilities, i.e., on a time average basis the volume corresponding to the calculation cell can be expected to have the quantity of charge calculated for the cell.

A typical initial charge distribution will have equal quantities of positive and negative charges, although systems having a net charge can studied if desired. As noted above, the initial charge distribution can be zero for all of the calculation cells, e.g., in cases where, for example, the system has or at some point during the calculation process will have a non-conservative field (see Section V(C) below) and/or an applied current source (see Section V(D) below). It should also be noted that a calculation cell having zero conductivity can have a finite quantity of charge, either initially or subsequently introduced. Such a quantity of charge can represent, for example, a quantity of fixed charge which, until removed, remains as a source of a temporally-constant electrical field which acts on the system as the calculations are performed.

Once established, the initial charge distribution is iterated forward in time by (1) calculating the net normal electric field at each face of each calculation cell and (2) using Ohm's law to calculate the quantity of charge that moves across each face in a time step. In particular, the net outward normal electric field at each face of each calculation cell is calculated using an equation of the form:

$$E_{nj} = \Sigma q_i r_{ij} \cdot n_j / (4\pi\varepsilon_0 r_{ij}^3), \qquad \text{Equation (1)}$$

where bold letters represent vectors, lower case letters represent the magnitude of vectors, · represents a dot product of two vectors, $r_{ij}$ is a vector from the center of the ith calculation cell to the center of the jth face and $r_{ij}$ is its magnitude, $q_i$ is the quantity of charge in coulombs in the ith calculation cell at the beginning of the time step, $n_j$ is the unit outward normal vector at the jth face, $\varepsilon_0$ is the dielectric constant of free space ($\varepsilon_0 \approx 8.85 \times 10^{-12}$ farads/meter in SI units), and the summation is over all of the calculation cells.

As can be seen, $E_{nj}$ is a function of $1/r_{ij}^2$ and thus through this equation, the computer-based computational tool calculates a spatial charge distribution using a $1/r^2$ law to express at least some of the fields of the system. As will be discussed below in Section V(C), in certain embodiments, the normal electric field at selected faces of selected calculation cells can have an additional component representing non-conservative fields which act on the system, e.g., fields of a concentration cell type arising from a difference in ionic concentrations across an ion-selective pore.

Once $E_{nj}$ is calculated, a quantity of charge is moved across the jth face based on an Ohm's law calculation of the form:

$$\Delta q = -\sigma E_{nj} s^2 \Delta t, \qquad \text{Equation (2)}$$

where $\Delta q$ is the quantity of charge in, for example, coulombs moved across the face and into the calculation cell in the time step (hence the minus sign since $E_{nj}$ is the net outward normal electric field), $\Delta t$ is the magnitude of the time step, $\sigma$ is the smaller of the calculation cell conductivities on the inside and outside of the jth face, and s is the length of an edge of the calculation cell so that $s^2$ is the area of a cell face.

Using Equations (1) and (2) and the values of the $q_i$'s at time t (i.e., the charge distribution at time t), a new set of $q_i$'s at time t+$\Delta t$ (i.e., a new charge distribution at time t+$\Delta t$) is calculated by summing for each calculation cell all of the Δq's for all of the cell's faces. The process begins with the initial charge distribution and is repeated until the desired information regarding the biological system is obtained with the charge distribution at the end of each time step becoming the starting distribution for the next time step. For example, in the case of a system which has a steady state, the process can be continued until the changes in the charge distribution between time steps drop to a desired small value, while in the case of a system which reaches a state of uniform decay (or growth), until all calculation cells substantially exhibit that decay (or growth).

Significantly, for dimensions of typical biological systems, the time course of charge distribution changes calculated using Equations (1) and (2) is a good representation of the actual time course of charge distribution changes in the system. See Preyer (2000) and Preyer (2002). In terms of understanding biological systems this is an important advantage of the direct calculation of charge distributions approach since it can provide important insights into the processing of information in biological systems.

In practice, it has been found that the calculation process can become unstable if Δt is made too small. For systems of the type examined in the examples presented below, this instability was found to arise when the σΔt product exceeded about $4 \times 10^{-12}$ seconds-siemens/meter. In general, it is desirable to keep Δt as large as possible so as to reduce overall computation time. Accordingly, a practical approach is to increase Δt until the instability is observed and then back off slightly so as to both avoid the instability and minimize the overall computation time.

Another effective approach for reducing overall computation time is to apply Equations (1) and (2) to a subset of the calculation cells and then use symmetry to determine the values of the $q_i$'s for the remaining calculation cells.

For example, in Example 1 below, a square pore is located at the center of a square patch of membrane, and the initial charge distribution is that of equal and opposite quantities of charge on either side of the membrane. For this highly symmetric case, $q_i$ values only need to be calculated for ⅛th of the calculation cells (e.g., with reference to FIG. 4, for the left, forward quadrant on the positive side of the midplane of the membrane), with the remaining $q_i$ values being immediately determined by symmetry (e.g., those in the right, forward quadrant on the positive side of the midplane of the membrane will have the values of the left forward quadrant reflected through the plane dividing those quadrants; those in the right and left rearward quadrants on the positive side of the midplane of the membrane will have the values of the corresponding forward quadrants reflected through the plane dividing the forward and rearward quadrants; and those on the negative side of the midplane of the membrane will have the values of the corresponding calculation cells on the positive side of the midplane reflected through the midplane and multiplied by −1). The same 8-fold symmetry was used in the calculations of Examples 2 and 3.

Corresponding symmetry strategies can be used for systems having less symmetry than that of Examples 1-3. It should be noted that for each calculation cell whose value is not determined by symmetry, the $q_i$ values at the beginning of the time step for the entire set of calculation cells are used in the evaluation of Equation (1), i.e., the summation in Equation (1) is still over all of the calculation cells. The savings in computation time based on symmetry arises from the fact that Equations (1) and (2) only need to be evaluated for a subset of the calculation cells, but for that subset all of the $q_i$ values, including those determined in the last time step using symmetry, are employed.

Figure 1A:
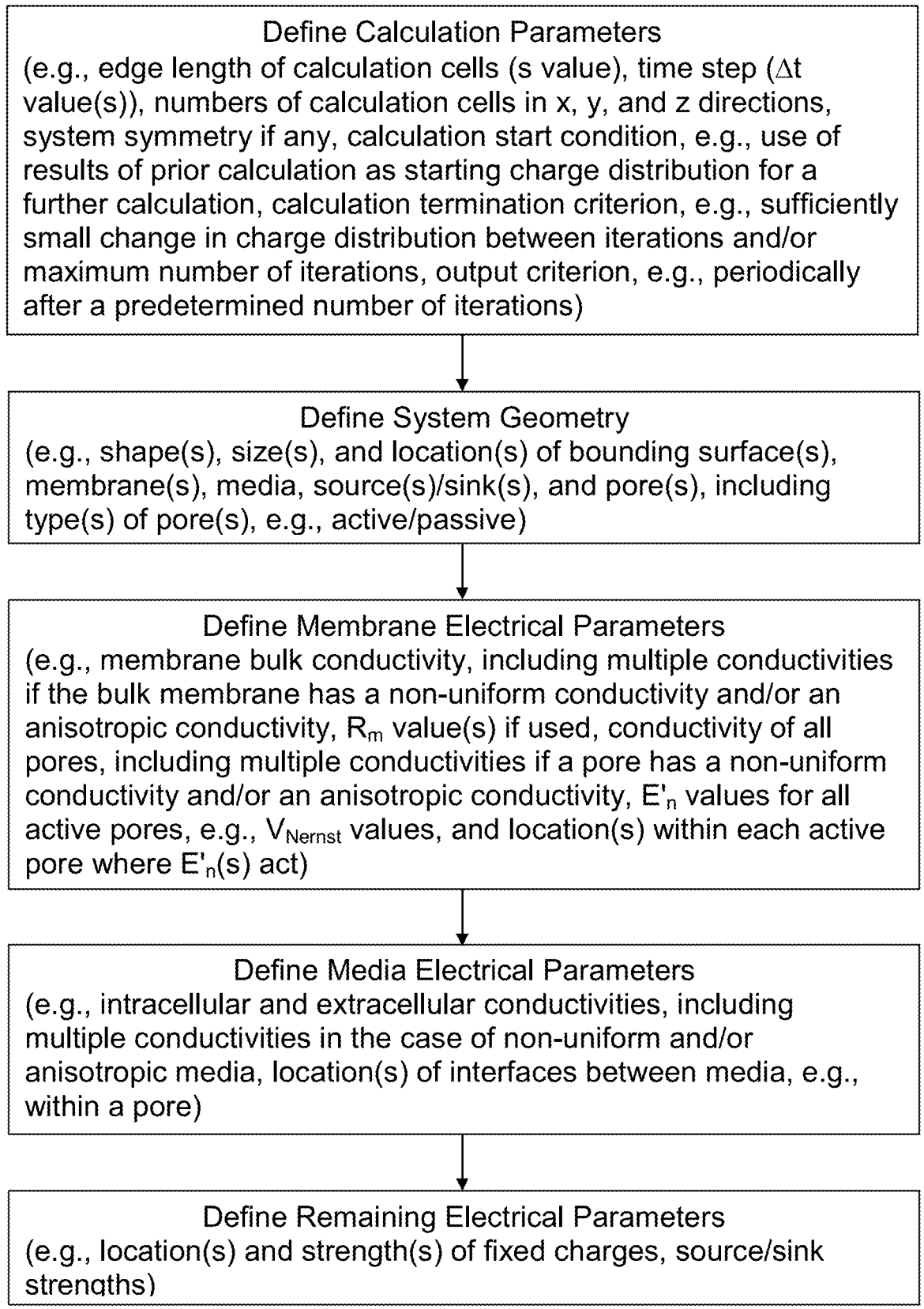

FIG. 1 sets forth a representative flow chart for setting up problems (FIG. 1A) and for calculating charge distributions and outputting results to a display and/or a storage device (FIG. 1). The flow charts of FIG. 1 are, of course, merely provided for purposes of illustrating an embodiment of the invention and are not intended to limit the scope of the invention as defined by the claims in any manner. As just one example, variables other than those used in FIG. 1A can be used to define the problem to be solved and the order in which the variables are defined need not be that shown in FIG. 1A.

The steps set forth in the flow charts of FIG. 1 or in other flow charts developed based on the present disclosure can be readily implemented using a variety of computer equipment and a variety of programming languages, e.g., FORTRAN 95, which is well-suited for scientific calculations. In this regard, as is typical for scientific calculations, the charge distributions of the invention will normally be determined in double precision. Other programming languages that can be used in the practice of the invention include, without limitation, BASIC, PASCAL, C, C++, and the like.

Output from the calculation process can be in electronic and/or hard copy form, and can be displayed in a variety of formats, including in tabular and graphical form. For example, graphs, including topographical graphs, can be prepared using commercially available data presentation software such as MICROSOFT's EXCEL program and/or R.

Software embodiments of the computer-based computational tools of the invention can be distributed to users in a variety of forms, e.g., on diskette, CD, flash drive, etc., or can be made available for on-line use over the Internet. The software can operate on various computing platforms, including personal computers, workstations, mainframes, supercomputers, etc. The computer-based computational tools are particularly well-suited for use with personal computers and as illustrated by the examples presented below are able to analyze a variety of electrophysiologically significant problems in reasonable amounts of time.

As just one example, the computations of Example 1 below were obtained using a three dimensional grid composed of 25×25×35 calculation cells. With a PENTIUM® 4, 3.8 GHz processor and taking advantage of the system's 8-fold symmetry, the processing time for a single iteration was approximately 3 seconds. Thousands of iterations could thus be performed in just a few hours using widely-available and relatively inexpensive equipment. Of course, if desired, even shorter analysis times can be achieved through code optimization, more powerful equipment, and/or through the use of parallel processing.

B. Biological Membranes

As discussed above, the present invention is concerned with biological membranes which have at least two regions with different electrical properties.

Typically, the difference between the electrical properties of the two regions will involve at least a difference in conductivity, with one region, e.g., the bulk of the membrane, having a low conductivity (e.g., $\sigma_1$), and one or more other regions, e.g., one or more pores or channels (hereinafter referred to generically as "pores," "pore(s)," or a "pore"), having a higher conductivity (e.g., $\sigma_2$ or, more generally, $\sigma_{2i}$, where i indicates the ith pore or a portion thereof in cases where the pore comprises a plurality of segments having different conductivities). The conductivity of the bulk membrane will typically be constant over time, although a time varying bulk conductivity may be useful in some applications of the invention. In many cases, the conductivity of the bulk membrane will be sufficiently low compared to that of the pore(s) so that it can be set equal to zero without significantly changing the calculated charge distribution.

While the conductivity of the bulk membrane will typically be constant in time, a time-varying conductivity for the pore(s) will often be of value in various applications of the invention. As just one example, the Hodgkin-Huxley equations, including variations thereof developed subsequent to Hodgkin's and Huxley's original work, can be used to describe changes in the conductivity of a pore over time. Thus, in an application of the invention to a study of a potassium pore(s), one could use Hodgkin-Huxley potassium kinetics, while for a sodium pore(s), one could use sodium kinetics.

It should be noted that the time steps used to calculate charge distributions (see Section V(A) above) will typically be much shorter than the time constants of the Hodgkin-Huxley equations (and other models for the conductivities of pore(s)), e.g., picoseconds versus milliseconds. Accordingly, in some applications of the invention, it may be desirable to treat the conductivity of a pore as a series of conductivity step changes, especially if the portion of the spatial charge distribution most strongly affected by changes in the conductivity of the pore (which may be the entire distribution depending on the particulars of the system being analyzed) relaxes faster (e.g., achieves a steady state or a simple RC growth or decay) in a relatively small fraction of a conductivity step. In this way, the calculation can jump forward (extrapolate forward) to the next conductivity step once the spatial charge distribution has sufficiently relaxed from the last conductivity change, thus reducing the number of charge distribution iterations needed to compute the overall behavior of the system.

Figure 2A:
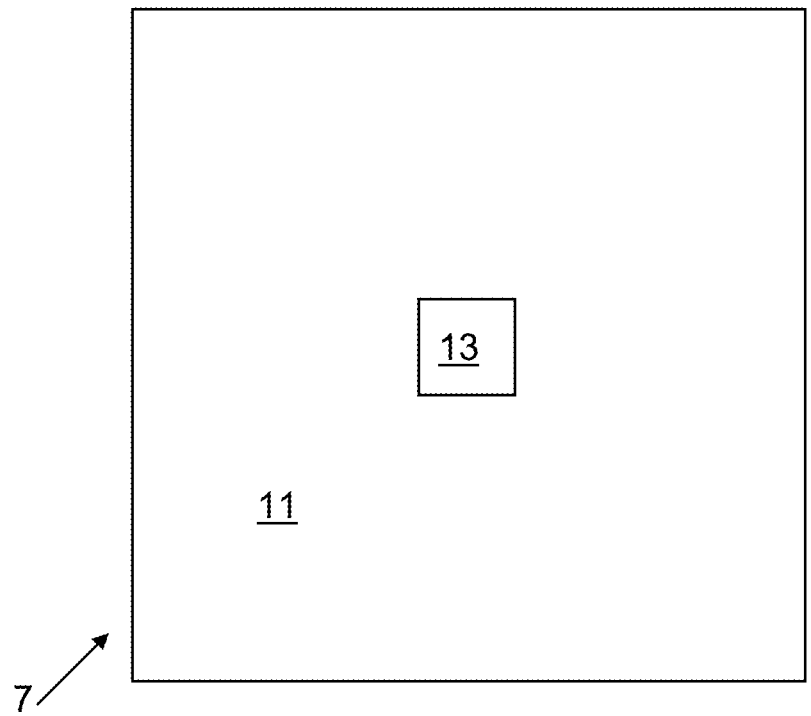
Figure 2B:
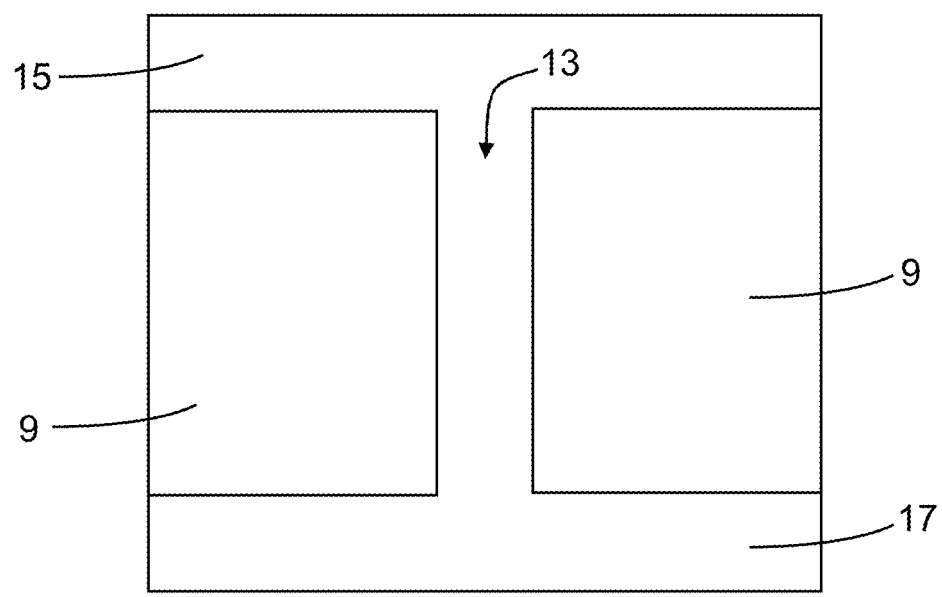

FIG. 2A is a top view and FIG. 2B is a cross-sectional view of a patch 7 of a biological membrane 9 having two regions 11 and 13 of different conductivities. Region 11 is bulk membrane having conductivity $\sigma_{r1}$ and region 13 is a pore having conductivity $\sigma_{r2}$, where $\sigma_{r1} < \sigma_{r2}$.

As shown in FIG. 2A, patch 7 has a square configuration, although it could have a variety of other shapes, e.g., triangular, rectangular, polygonal, etc. Similarly, pore 13 has a square configuration, although again it could have a variety of other shapes.

As discussed above in Section V(A), in their preferred embodiments, the computer-based computational tools of the invention employ cubic-shaped calculation cells and thus pores, membrane patches, cells, tissues, bathing solutions, and the like will have bounding edges formed of straight line segments. If desired, bounding edges having a curved shape can be readily generated using the straight line segments of the cubic calculation cells, the smoothness of the curve being a function of the number of segments used. However, as illustrated by the examples presented below, numerous phenomena, many of which were heretofore unknown, can be studied using the computer-based computational tools of the invention and rectilinear geometries formed by three-dimensional assemblies of cubic-shaped calculation cells.

Surrounding patch 7 are extracellular and intracellular media 15 and 17 (extracellular and intracellular volumes 15 and 17) having conductivities $\sigma_{ext}$ and $\sigma_{int}$. Depending upon the system being studied, conductivities $\sigma_{ext}$ and $\sigma_{int}$ can be the same or different. Also, rather than having a single conductivity, the extracellular and/or intracellular volumes can be segmented into regions of different conductivities. The same is true of membrane conductivities, e.g., the conductivity of a pore may vary between the pore's extracellular and intracellular ends, as can the bulk membrane. For both the surrounding media and the membrane, the conductivities can be anisotropic.

Importantly, during current flow, quantities of charges accumulate at interfaces between regions having different conductivities. Moreover, these "primary" interface charge distributions can be associated with "secondary" charge distributions (also referred to herein as "turning charges"). For example, as illustrated in Example 3 below, it has been found that applying current to a patch of membrane which includes a pore having an interface between extracellular and intracellular media of different conductivities at the pore's midplane generates both a primary charge distribution at the interface and a secondary charge distribution in the form of a ring of charge surrounding the pore on the surface of the membrane on the low conductivity side of the interface (see the dashed curve of FIG. 19). Since biological membranes often include information processing molecules, e.g., ligand binding proteins, in regions adjacent to pores, the locations of these secondary charge distributions suggest that they play a role in pore function.

In practice, the effects produced by conductivity differences are of particular interest because the conductivities of extracellular and intracellular media can be readily changed experimentally, e.g., in connection with patch clamp experiments. Consequently, comparisons can be made between (a) experimental data obtained using different combinations of extracellular and intracellular conductivities and (b) the predicted charge distributions, obtained using the computer-based computational tools of the invention, for those combinations. In this way, mechanisms known or believed to be involved in the operation of pores can be confirmed and heretofore unknown mechanisms can be discovered.

Further interplay between experimental studies and the computer-based computational tools of the invention can, for example, be based on adding one or more chemicals, e.g., ions, polymers, drugs, and/or toxins, known or suspected to affect pore function to the extracellular and/or intracellular media. Combinations of media conductivity changes, chemical treatments, and, for example, applied currents (see Section V(D) below) can provide experimental protocols with sufficient adjustable parameters to uncover mechanisms involved in disease states as well as those involved in the treatment or amelioration of disease states. Combinations of these approaches with genetic engineering techniques, e.g., specific amino acid changes in pore proteins, provide even further possibilities for research into pore function.

The membrane configuration of FIG. 2 captures the basic geometry of a patch clamp experiment, i.e., as in a patch clamp experiment, an isolated patch of membrane is bathed by two solutions whose compositions can be individually controlled. As illustrated in FIG. 17 and discussed in Section V(D) below, in accordance with certain embodiments of the invention, current can be applied across the membrane and the magnitude and/or direction of the current can be adjusted based on calculated potential differences between selected points in the system, e.g., between a representative point on the intracellular side of the membrane and one on the extracellular side to give a measure of the transmembrane potential across the membrane patch. As illustrated in FIG. 11 and discussed in Section V(E) below, the perimeter of the bulk membrane at the interface between the membrane and the surrounding insulating wall of the system can be given a finite conductivity corresponding to the leakage path through the seal between a patch of membrane and the walls of a microelectrode known to exist in practice during patch clamp experiments. With these additions, the FIG. 2 system can be used to provide insights into the strengths and weaknesses of the patch clamp technique previously unknown in the art. With those insights, improvements to the technique can be developed.

Studies using the geometry of FIG. 2 also allow basic pore phenomena to be investigated without the complications associated with more complicated geometries. This allows researchers to obtain a thorough grounding in the fundamentals of pore operation, as well as providing a teaching tool for explaining pore phenomena to students.

Although the FIG. 2 geometry has many advantages, it will often be desirable to study more complicated geometries such as complete biological cells or organelles whose membranes form a closed surface. Such geometries can be studied by assembling membrane sections until the desired geometry has been generated. As discussed above, such assembling can produced curved geometries if desired.

However, representing the entire thickness of the membrane in detail can lead to large numbers of calculation cells. This problem arises because of the thinness of biological membranes which means that if a substantial number of calculation cells is used to represent the thickness of the membrane even larger numbers are needed to represent the intracellular space within a closed cell or organelle whose dimensions are many times greater than a membrane's thickness. For the same reason, large numbers of calculation cells will be needed in many cases of interest to describe the extracellular space surrounding a cell or organelle.

This problem can be addressed by reducing the number of calculation cells dedicated to describing the membrane. For example, the membrane can be described by just a few layers of calculation cells, e.g., in the limit, a single layer of calculation cells having an edge length equal to the desired thickness of the membrane. However, for some problems, even the use of only a single layer of calculation cells to describe the membrane may not reduce the overall number of calculation cells to an acceptable level in view of processor speed and available calculation time. To address this problem, in accordance with certain embodiments, instead of using calculation cells to represent the membrane, the computer-based computational tools of the invention use faces of calculation cells for this purpose.

Figure 3A:
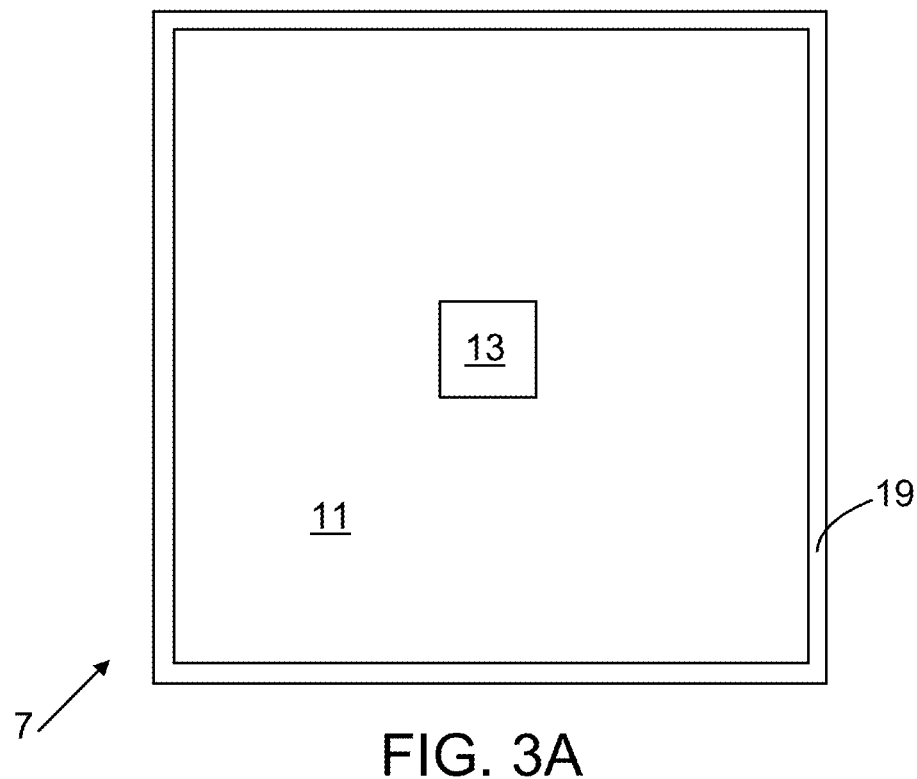
Figure 3B:
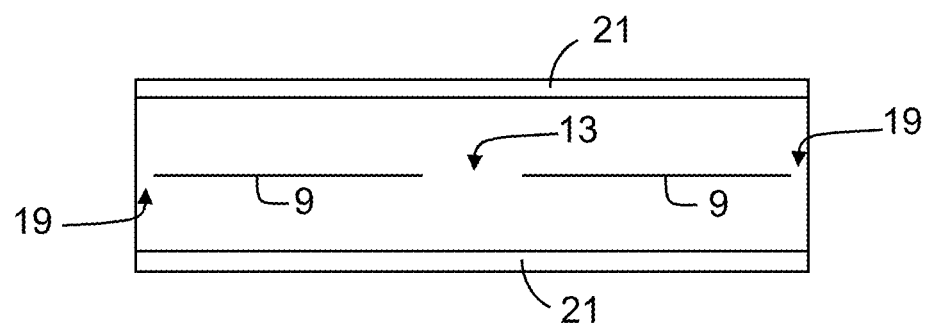

FIG. 3 illustrates a system of this type where membrane 9 has been reduced in thickness to a mathematical surface. As shown in this figure, a pore 13 and a perimeter path 19 (see Section V(E) below) pass through the membrane. For the calculation cell faces located at the membrane, instead of using the smaller of the two conductivities on either side of the face as the value of σ in Equation (2), an effective or average conductivity $\sigma_E$ is used, where $\sigma_E$ is selected based on the desired local conductivity (resistivity) of the membrane.

Values of $\sigma_E$ can be related to the specific resistance values in ohms-meters$^2$ often used to describe the resistance of a biological membrane as follows. For a membrane having a specific resistance $R_m$, the total resistance R of a face of a calculation cell of area $s^2$ is $R_m/s^2$. For a potential difference V between the centers of the two calculation cells which share the face, the total current I through the face, from Ohm's law, equals V/R. Substituting the above value for R gives $I=Vs^2/R_m$.

The total current through the face is also given by $Js^2$, where J is the current density at the face, assumed to be uniform over the face. Again by Ohm's law, J can be written: $J=\sigma_E E_E$, where $E_E$ is an effective electric field associated with current passing through the face. For a potential difference V between the centers of the calculation cells on either side of the face, the average electric field between the centers can be approximated as V/s, where s is the distance between the centers. Using this field as $E_E$ gives: $J=\sigma_E V/s$, or, in terms of total current, $I=Js^2=\sigma_E Vs$.

Equating the two expressions for I gives $Vs^2/R_m=\sigma_E Vs$, or $\sigma_E=s/R_m$. Thus, instead of using Equation (2), for faces of calculation cells which represent biological membranes, the following modified equation can be used:

$$\Delta q = -E_{nj} s^3 \Delta t / R_m \qquad \text{Equation (3)}$$

where $R_m$ can, for example, take on different values at different locations to represent bulk membrane, pores, synapses, gap junctions, or the like.

It should be noted that the face approach for representing biological membranes frees the size of the calculation cell from the thickness of the membrane. Thus, the edge of the calculation cell can be much larger than, for example, a single membrane thickness. However, it should also be noted that the specific capacitance of the membrane will decrease as the calculation cell size increases. To a first approximation, the specific capacitance varies as one over the distance between the centers of the calculation cells on either side of the face, i.e., the specific capacitance varies approximately as 1/s. Thus, as the size of the calculation cell increases, the specific capacitance decreases so that the time course observed using the computer-based computational tools of the invention will be faster than the actual time course. However, as discussed below in Section V(F), improved approximations to the actual time course can be obtained through extrapolation, scaling, and/or interpolation techniques.

Substantial reductions in the number of calculation cells used to represent the thickness of the membrane, as well as the use of the face approach for representing the membrane, does of course mean that the computer-based computational tools of the invention will provide less detail regarding phenomena occurring at locations where the electrical properties of the membrane change. For example, the primary and secondary charge distributions discussed above can become merged under these conditions. Nevertheless, for many problems, the trade-off is worthwhile since it can facilitate the study of more complex geometries. And, the detailed behavior in the vicinity of electrical property changes can still be studied by representing the effects of distant geometries through perimeter conductivities and/or perimeter non-conservative fields as discussed below in Section V(E).

The σ's, $R_m$'s, and other values used in applications of the computer-based computational tools of the invention (e.g., $V_{Nernst}$ values; see Section V(C) below) will, of course, depend on the particular biological system being studied. Representative values and the techniques by which the values were measured can be found in various textbooks, e.g., Hille (2001), Plonsey (1969), and Plonsey and Barr (2000), as well as in original research papers. The examples set forth below illustrate the use of typical values found in these sources. In particular, these examples illustrate the transformation of these previously-measured electrophysiological values into a form that is more useful for interpreting and/or visualizing the physiological phenomena which produced the values.

Rather than using previously-measured values, when the computer-based computational tools of the invention are used in connection with an on-going electrophysiological experiment or series of experiments, the values used in the computations can be those measured during the experiment(s), e.g., voltages and/or currents measured during voltage clamp, current clamp, or similar experiments. The computations can be made in real time as the experiments are being conducted or measurements can be collected during the experiments and the computer-based computational tools applied thereafter. In either case, the transformation of the experimental data by the computer-based computational tools is used to interpret and/or visualize the data, and can also be used as a guide to further experiments.

C. Non-Conservative Fields

In addition to conductivity, the regions of the membrane can vary in terms of the presence or absence of non-conservative fields, where, as used herein, a non-conservative field is a field which originates from a source whose effect on the charge distribution of the system is not represented by a $1/r^2$ law.

For example, as is well known, many biological pores are selective for a particular type of ion, e.g., sodium, potassium, or calcium, and because the concentration of the ion is different on the extracellular and intracellular sides of the membrane, a Nernst potential will be generated with the side having the higher concentration of the ion developing a charge distribution opposite to that of the ion so that at equilibrium the difference in chemical potential between the two sides of the membrane is balanced by a difference in electrical potential.

The ion selectivity in combination with the differences in ion concentrations between the two sides of the membrane (differences in chemical potential) produces a localized non-conservative field (chemical field) which can change the overall spatial charge distribution. The locus of this non-conservative field is at the interface between the media where the ion selectivity takes place. A variety of models have been developed for the ion selectivity of biological pores (see, for example, Hille (2001)) which place the selectivity at various locations within the pore between its extracellular and intracellular ends.

In terms of the computer-based computational tools of the present invention, non-conservative fields can be included in the system by modifying Equation (2) to include an additional term to represent movement of a quantity of charge across a face as a result of fields other than those of the overall charge distribution that produces $E_{nj}$. Designating the net outward field at the jth face due to the non-conservative fields as $E'_{nj}$, we have:

$$\Delta q = -\sigma(E_{nj} + E'_{nj})s^2 \Delta t. \qquad \text{Equation (4)}$$

Typically, $E'_{nj}$ will be zero for most of the faces of the calculation cells. It will be finite for selected faces associated with, for example, an ion selective pore. For such a pore, $E'_{nj}$ can, for example, be finite for the faces along the midplane of the pore, or at some other location between the extracellular and intracellular ends of the pore. Alternatively, faces lying at multiple planes between the extracellular and intracellular sides of the pore can be used to represent the non-conservative field which an ion selective pore imposes on ions passing through the pore.

For example, it can be assumed that the change in concentration of the ion which can pass through the pore between the extracellular and intracellular media takes place in a series of steps corresponding to the series of calculation cells used to represent the thickness of the membrane. For this case, an $E'_{nj}$ field will exist at multiple calculation faces between the extracellular and intracellular sides of the pore, the magnitudes of which will depend on the particular concentration profile assumed to exist within the membrane. A variety of concentration profiles can be analyzed in this manner, such as, linear, linear with two or more slopes, linear with one or more flat portions, curved, etc.

The magnitude and direction of the non-conservative field can be selected based on, for example, the Nernst potential difference predicted for the ion selectivity of the pore and the ionic compositions of the intracellular and extracellular media of the system being studied. Designating that potential difference (intracellular minus extracellular) as $V_{Nernst}$, and assuming that the non-conservative field corresponding to this potential acts at a single plane within the pore as opposed to multiple planes, i.e., assuming the change in concentration of the ion occurs across a single plane, $E'_{nj}$ can be written:

$$E'_{nj} = -V_{Nernst}/s, \qquad \text{Equation (5)}$$

where the unit normal n is assumed to point from the intracellular side of the face towards the extracellular side, i.e., the calculation cell is on the intracellular side of the face, or $$E'_{nj} = +V_{Nernst}/s, \qquad \text{Equation (6)}$$

if the unit normal points in the opposite direction, i.e., if the calculation is performed for the calculation cell on the extracellular side of the face. (Note that in practice, $E_{nj}$, $E'_{nj}$, and $\Delta q$ only need to be evaluated once for one side of a face since to maintain charge conservation, the quantity of charge exchanged between two calculation cells through a shared face must be equal and opposite, e.g., if a calculation cell on the intracellular side of a face receives $\Delta q$ charges from the calculation cell on the extracellular side of the face in a time step then the extracellular side calculation cell must lose $\Delta q$ charges to the intracellular side calculations cell in that time step so that there is no net creation or destruction of the total quantity of charge in the system.)

The minus sign of Equation (5) and the plus sign of Equation (6) can be understood as follows. If $V_{Nernst}$ is negative, e.g., for a potassium-selective pore where the intracellular concentration of potassium is greater than the extracellular concentration, the non-conservative field moves positive ions (potassium ions) from the intracellular side of the membrane to the extracellular side and thus the direction of that field is outward, i.e., $E'_{nj}$ should be positive/negative for the intracellular/extracellular calculation cell so that $\Delta q$ due to $E'_{nj}$ in Equation (4) is negative/positive for those calculation cells. The minus/plus sign in Equation (5)/Equation (6) gives $E'_{nj}$ this orientation for the calculation cell on the intracellular/extracellular side of the membrane.

For cases where the change in ion concentration between the extracellular and intracellular media is assumed to take place in a series of steps (see above), Equations (5) and (6) can be used at each face for which there is a concentration change with the value of $V_{Nernst}$ being calculated for the assumed concentration change across the face.

Non-conservative fields can be also be used in the embodiments of the invention where, instead of using one or more calculations cells to represent the thickness of the membrane, the interface between a pair of calculation cells is used for this purpose. Equation (3) then becomes:

$$\Delta q = -(E_{nj} + E'_{nj})s^3 \Delta t/R_m, \qquad \text{Equation (7)}$$

where again Equations (5) and (6) can be used to determine the magnitude and orientation of $E'_{nj}$ for non-conservative fields associated with an ion-selective pore between extracellular and intracellular media having different concentrations of the permeant ion.

D. Applied Currents

As noted above, one of the important tools employed in experimental studies of electrophysiological systems is the application of current to the system. Such currents can be applied on a single side of a membrane, e.g., between two extracellular locations, or across the membrane. Both current clamp and voltage clamp configurations are used depending on the particular phenomenon being studied. Applied currents are also important in the stimulation of cells, both in experimental and clinical settings, e.g., in heart pacemakers and prosthetic orthopedic, vision, and other types of devices. Applied currents are also used as part of the drug discovery process. See, for example, Huang et al. (2006) and U.S. Patent Application Publications Nos. US 2006/0216690 and US 2006/0252111.

Applied currents can be incorporated in the computer-based computational tools of the present invention by introducing, at each time step, a selected quantity of charge into selected calculation cells (a first zone of calculation cells) and removing the same quantity of charge from other calculation cells (a second zone of calculation cells). (Note that the calculation cells making up a zone need not be contiguous, i.e., the current can be introduced and/or removed from the system at multiple locations.) By introducing and removing the same quantity of charge at the two zones, the net quantity of charge in the system (typically, zero) is held constant. If a net quantity of charge is desired, it can be introduced at the beginning of the computation process or can be introduced later by making the total quantity of charge introduced at the calculation cells of the first zone larger than the quantity removed at the calculation cells of the second zone (or vice versa) for a period of time A current clamp configuration is produced when the quantity of charge introduced and removed at the first and second zones is held constant over time. To represent a voltage clamp, a difference in electrical potential between two locations, e.g., an intracellular location and an extracellular location, can be calculated at each time step (or at intervals comprising a plurality of time steps) and used to change the quantity of charge introduced/removed at the first and second zones so that the potential difference is moved towards a specified value, i.e., the calculated potential difference is used in a feedback loop for adjusting the magnitude/direction of the quantity of charge introduced/removed from the system at the first and second zones. The feedback loop can include feedback parameters, time constants, and the like which mimic those of experimental equipment used in voltage clamp experiments, e.g., equipment of the type sold under the AXON CNS brand name by the MDS Analytical Technologies Division of MDS Inc., Toronto, Canada.

The difference in electrical potentials used in this feedback process can be calculated from a charge distribution (set of $q_i$ values) determined from Equation (1) and one or more of Equations (2)-(7) at any particular point in time as follows. Designating the potentials at the two locations as $\Phi_1$ and $\Phi_2$, the difference in potential can be written:

$$\Delta\Phi = \Sigma q_i/(4\pi\varepsilon_0 r_{i1}) - \Sigma q_i/(4\pi\varepsilon_0 r_{i2}), \quad \text{Equation (8)}$$

where $r_{i1}$ and $r_{i2}$ are, respectively, the magnitudes of distances between quantity of charge $q_i$ and the first and second locations at which the potential is being evaluated and, as in Equation (1), the sums are over all the quantities of charge in the system.

A convenient location for calculating potential values is often at the center of a calculation cell. For this location, r becomes zero for the quantity of charge q of the chosen cell (the "self-term"), and thus Equation (8) needs to be modified to avoid this singularity. This can be done by considering the quantity of charge of the self-term calculation cell as being uniformly distributed over the volume of the cell. The potential at the center of the cube can then be evaluated analytically as:

$$\Phi = 2.38 q/(4\pi\varepsilon_0 s), \quad \text{Equation (9)}$$

where s is the length of the edge of the cube and the potential at infinity is assumed to be zero. By using Equation (9) for the self-term cells in the Equation (8) calculation, the singularity problem is removed. Alternatively, the singularity problem can be avoided by picking locations for evaluating potentials which are not located at the centers of calculation cells.

It should be noted that the self-term singularity problem does not arise for Equation (1) because the normal electrical field calculated by that equation is located at a face of a calculation cell, not at its center. Thus, the smallest $r_{ij}$ value used in Equation (1) is s/2, not zero.

However, as noted by Preyer (2000), some error is introduced by the discretation process as evidenced by the fact that at steady state, all of the quantities of charge in a conductor do not end up in calculation cells at the edges of the conductor. The drop-off in charge quantities is, however, quite rapid, typically being around 90% for each inward step away from the edge, e.g., if the calculation cell at the edge of a conductor has 100 elementary charges, the next inward cell will typically have around 10 charges, the one after that around 1 charge, and so forth. For this reason, in practice, conductive paths having dimensions in all directions of at least 5 calculation cells have been found preferable for many calculations. In this way, interactions between the edges of a conductor as a result of discretation errors can be minimized.

E. Perimeters

As mentioned above, one of the most common preparations used to study electrophysiological phenomena is the patch clamp. A characteristic of this preparation is that it includes a leakage path between the extracellular and intracellular media along the perimeter of the patch (the so-called gigaseal). This path can be represented in the computer-based computational tools of the invention by assigning a higher conductivity to selected computational cells along the perimeter of a piece of membrane. See, for example, Example 2 below.

In addition to its use in analyzing patch clamp experiments, the perimeter of a piece of membrane can be used to represent the effects of neighboring membrane pieces without the need to explicitly include those neighboring pieces in the calculation process. This can result in a substantial savings in computation time.

For example, if a piece of membrane (the central piece or inner region) is surrounded by other pieces (the outer region) which, for example, include one or more low resistance pores, as viewed from the perspective of the central piece, those other pieces represent a path for current flow between the extracellular and intracellular sides of the central piece. Rather than using calculation cells to represent the surrounding pieces, their effects on the central piece can be embodied in a higher conductivity around the perimeter of the central piece, the magnitude of which is chosen to represent the conductivity of the pores of the outer pieces as well as the resistance of the extracellular and intracellular media through which current must pass to reach those outer pores from the central piece.

In addition to a higher conductivity, the perimeter calculation cells can include non-conservative fields in accordance with Section V(C) above to represent the non-conservative fields associated with the surrounding pieces, e.g., active sodium pores surrounding an active potassium pore or vice versa. To provide even greater flexibility in representing the environment surrounding a particular piece of membrane, the properties of the perimeter calculation cells, including their conductivity and non-conservative field properties, can be different in different directions.

For example, a long thin structure can be represented by high conductivities for the perimeters along two edges of, for example, a rectangular piece of membrane and low conductivities for the other two edges. For this example, the low conductivity edges would be parallel to the long axis of the structure and the high conductivity edges would be orthogonal to that axis. As a further variation, the high conductivity edges could have different conductivities and/ or different non-conservative fields to, for example, represent a soma at one end of the structure and a synapse at the other end. Numerous other combinations and variations for perimeter calculation cells will be evident to persons of ordinary skill in the art from the foregoing representative examples.

In general, only a single layer of perimeter calculation cells will be needed to represent the effects of the surrounding pieces of membrane, but multiple perimeter layers can be used if desired. The perimeter approach can also be extended to membranes having non-planar configurations. For example, a tubular-shaped membrane of a given length can have perimeter calculation cells at one or both of its ends to represent the effects of a longer tubular structure of which it is a part.

For both the planar and non-planar cases, the portion of the membrane explicitly represented by calculation cells (or interfaces between calculation cells) should be large enough so that the presence of the insulating walls surrounding the calculation space does not produce unacceptable artifacts in the charge distribution being calculated. This can be easily checked by repeating the calculation with a somewhat larger and/or somewhat smaller calculation space and examining/ comparing the results for the presence of substantial differences at locations spaced from the walls, e.g., near the center of the space.

F. Extrapolation, Scaling, Superposition, and Interpolation

The perimeter calculation cell approach discussed immediately above is an effective way of reducing the number of calculation cells and thus the calculation time needed to analyze electrophysiological systems. Other approaches for reducing calculation time include extrapolation, scaling, superposition, and interpolation.

In extrapolation, a series of calculations are performed during which a parameter, e.g., the area of the piece of membrane, is systematically varied over a range (the test range) for which the computational time for each calculation is reasonably short. A variable of interest, e.g., a system's overall time constant, the maximum surface charge density in the vicinity of a pore, the surface charge density at locations distant from a pore, the maximum transmembrane potential across a membrane, etc., is determined for each calculation.

A fit is then performed relating the values of the variable of interest to the values of the varied parameter. In many cases, a linear or exponential fit will be suitable, although in some cases more complicated fits will be needed. For example, the variable may change with the parameter over a portion of the tested range of the parameter and then become, for example, independent of the parameter for another portion of the tested range. Using the fit, values for the variable of interest can be determined for values of the varied parameter outside of the range used for the fit. In particular, values of the variable of interest can be obtained for values of the varied parameter that would involve unacceptably long computation times.

Scaling can also be used to transform data determined for one set of parameters to a different set of parameters. For example, scaling of the conductivities of a system does not change the system's spatial charge distribution (although, depending on the problem, the magnitude of the charge distribution may change), but does change the system's temporal behavior, i.e., the temporal response varies linearly with a multiplicative change in all of the conductivities of the system. Thus, if the geometry is held constant, the time response determined for one set of conductivities can be transformed to a time response for a scaled set of conductivities by simply applying the same scale factor to the time response.

Estimates of time constants for different pore/membrane combinations can also be obtained through scaling. Using the computer-based computational tools of the invention it has been determined that to first order, the time constant T of a piece of membrane having pores filled with a conductive medium of conductivity $6p$ where the pore is the primary resistance can be expressed as:

$$\tau \approx (\varepsilon_0/\sigma_p)/(D_p A_p), \quad \text{Equation (10)}$$

where $D_p$ is the pore density (e.g., pores per nm of membrane), $A_p$ is the pore area (e.g., in nm$^2$), and $\sigma_p$ and $A_p$ can, for example, be values for a singe pore or average values for a population of pores.

An examination of Equation (10) reveals that for a fixed number of pores, as the area of the membrane increases, the pore density decreases, and thus the time constant increases, as would be expected since the amount of membrane surface area that needs to be charged or discharged through the fixed number of pores has increased. Conversely, if the number of pores increases for a fixed membrane area, the pore density increases which decreases the time constant, again as would be expected since the number of paths through the membrane is now greater, thus lowering the resistance for charging or discharging a fixed area of membrane. Likewise, increases/decreases in the area of a pore $A_p$ for a fixed number of pores and a fixed membrane area, results in decreases/increases in the membrane time constant, as would be expected because again the resistance through the membrane is now lower/higher for given pore electrical properties. Finally, the $\varepsilon_0/\sigma_p$ ratio in the numerator of Equation (10) corresponds to the intrinsic relaxation time of the pore's conductive medium. As that relaxation time increases/decreases, the overall time constant of the pore/ membrane combination increases/decreases, again as would be expected.

Equation (10) is particularly useful in scaling temporal results obtained using small pieces of membrane, as is often desirable to reduce computation times. The temporal behavior of small membrane pieces are fast because of the small membrane areas which need to be charged/discharged. Using Equation (10), the temporal behavior for larger pieces of membrane can be readily predicted by simply scaling the pore density.

Superposition is another powerful tool for minimizing the number of calculations needed to analyze a particular system. For example, a system consisting of two spatially separated pores, each having a non-conservative field, which may be the same or different for the two pores, can be analyzed by first calculating the charge distribution produced by the first pore with its non-conservative field active and with the second pore's non-conservative field inactive (and with both pores having their active conductivities), and then calculating the charge distribution for the converse problem, i.e., the second pore active and the first pore inactive (again with both pores having their active conductivities).

Superimposing these two charge distributions gives the charge distribution for both pores active. Also, the charge distribution scales linearly with the strength of the non-conservative field and thus any desired combination of first pore/second pore active strengths can be readily determined through superimposition once the basic active/inactive charge distributions are known. A change in the conductivity of one or both of the pores, other than in connection with a scaling of all of the system's conductivities (see above), will, however, change the charge distribution and thus will require a new calculation.

A particularly important application of superposition is in connection with the application of applied currents, especially in the case of voltage clamp experiments. Both the charge distribution and potential distribution of the combination of an applied current and one or more active pores can be determined by superposition and thus once the potential difference due to the active pore(s) has been determined, the applied current needed to null out that potential difference (or set it to a desired value) can be determined from a separate calculation of the charge distribution produced by the applied current and its corresponding potential distribution for the system with the non-conservative fields associated with the pore inactivated. Since the charge and potential distributions scale linearly with the applied current, once the distributions are known, selecting the magnitude and sign of the applied current is straightforward.

As with other applications of superposition, the charge distribution produced by an applied current will change with changes in the conductance of the system's pore(s) and thus a series of calculations using different pore conductances will typically be needed to account for this effect. Interpolation of a fit to the results of the calculations, e.g., a piecewise linear fit, can be used to reduce the number of conductances for which a full calculation is performed. Similarly, interpolation can be used to determine the charge distribution due to a non-conservative field for different pore conductances. In addition to pore conductances, interpolation can also be used with perimeter conductances and media resistivities.

G. Examples

Without intending to limit its scope in any manner, the invention is further illustrated by the following representative examples.

Example 1

This example illustrates the use of the computer-based computational tools of the invention to determine charge distributions that cause current to enter a pore in a biological membrane.

Figure 5:
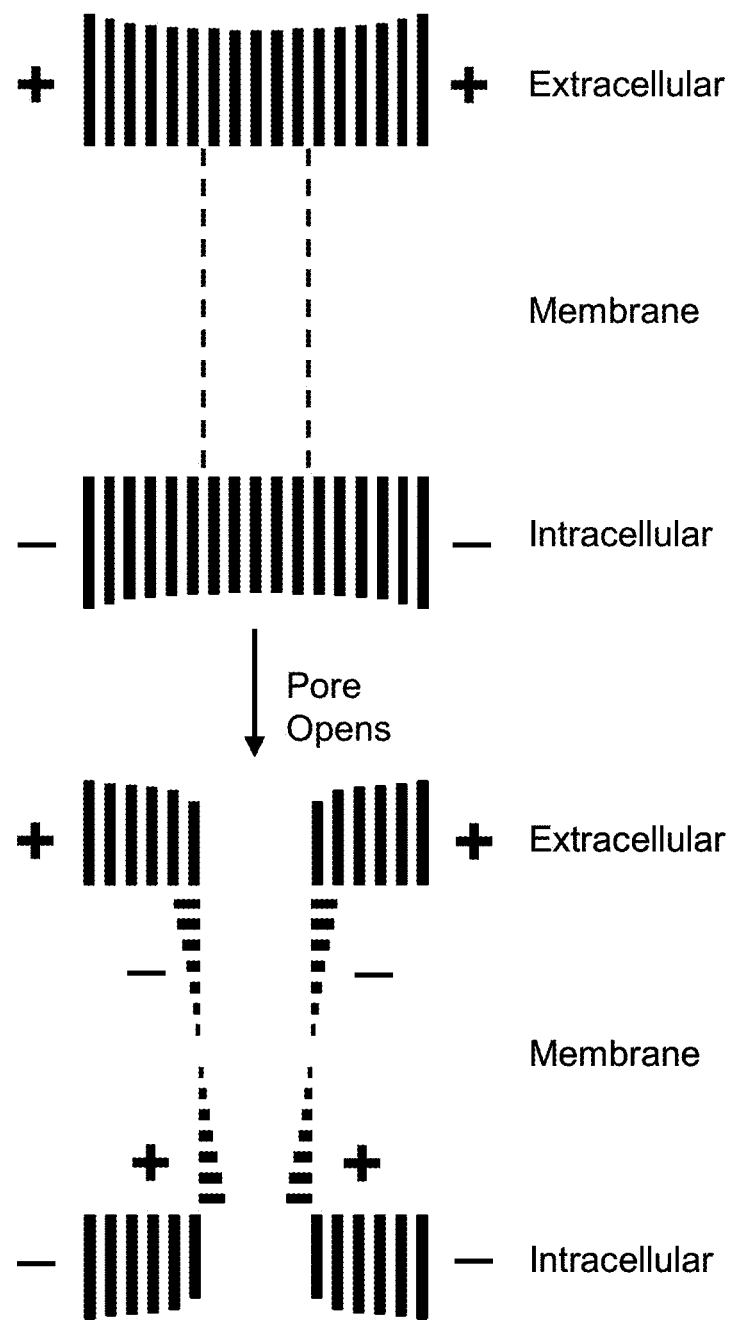
Figure 6:
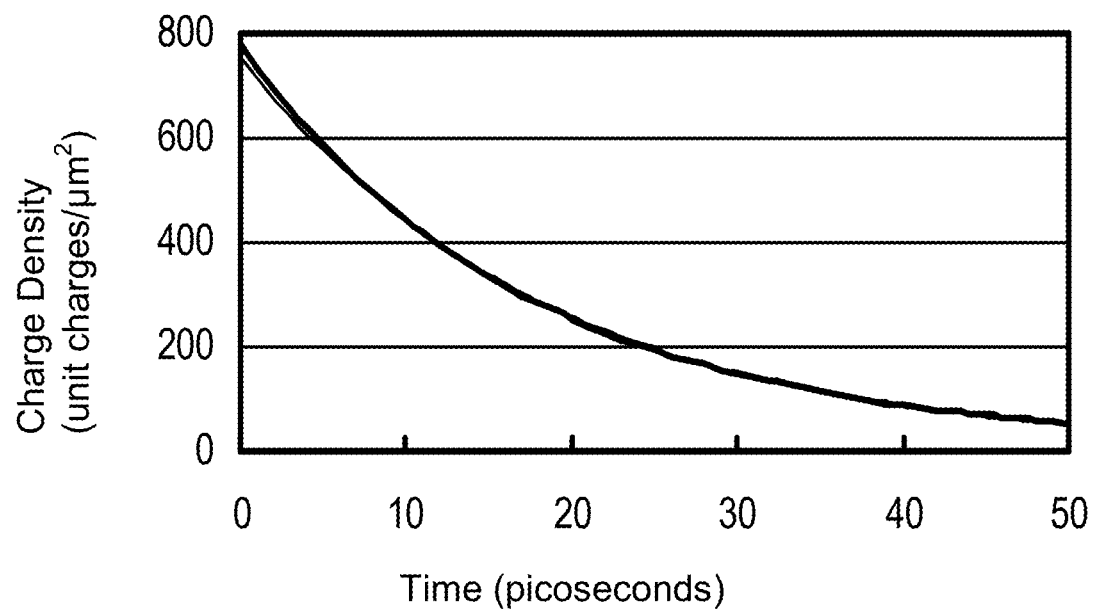
FIG. 6 shows the time course of charge decay at the "FIG. 6" point of FIG. 4. The time constant τ for the decay is 19 picoseconds which corresponds to the relaxation time ($\varepsilon_0/\sigma$) of the biological fluid, i.e., the extracellular and intracellular media.

The example demonstrates that: (1) the opening of a biological pore produces an initial rapid redistribution of charge in the vicinity of the pore followed by a slower steady decay of the overall charge distributions on either side of the membrane (i.e., the opening of a pore involves multiple time constants having substantially different values); and (2) as shown in FIG. 5, during the initial rapid phase, charges accumulate at the entrance and exit ends of the pore which have a sign opposite to that of the charges on the surrounding membrane surface (referred to herein as "current-turning charges").

Analogies to these current-turning charges can be found in the charge distributions postulated to exist in natural pores. In particular, FIGS. 11.11 and 17.3 of Hille (2001) show renditions of protein configurations which include charged amino acid residues whose signs and locations correspond to those shown herein to be involved in turning current into a pore.

FIG. 4 shows the configuration of the electrophysiological system for which the charge distributions were determined. A square patch of a planar membrane having an area of 100 Å×100 Å, a thickness of 60 Å, and zero conductivity was placed between two 40 Å layers of a biological fluid having a conductivity of 0.4 siemens/meter (resistivity=250 ohm-cm). The pore was assumed to be a square having 20 Å sides located at the center of the planar membrane and, when open, to be filled with the biological fluid. The pore dimensions and electrical parameters were based on Hille (2001), Chapter 4 of Plonsey and Barr (2000), and Islas and Sigworth (2001).

Charge distributions were determined using Equations (1) and (2) above. The overall volume was divided into 25×25×35 cells having an edge length (s value) of 4 Å. A time step ($\Delta t$) of 1 picosecond was used in the calculations. The system's 8-fold symmetry was used to reduce computation time. In addition, calculation cells having zero conductivity, i.e., those located within the bulk of the membrane, were skipped during the iterative process since their q values are zero at all times.

The analysis was performed in two steps. First, equal positive and negative charges were introduced on either side of an intact membrane without a pore. The system was then relaxed until charge motion ceased. The amount of charge was chosen so as to produce a transmembrane potential (($\Phi_i-\Phi_e$) of −100 millivolts.

In the second step, the fully relaxed solution of the first step was used as the starting point and the 20 Å×20 Å pore was introduced at the center of the membrane patch at t=0. The system was again relaxed with the computation being continued until steady state was reached in the sense that the charge distribution was decaying in accordance with the system's overall RC time constant.

FIG. 5 illustrates the manner in which the charge distribution changes as a result of the opening of the pore. The top portion of the figure shows the charge distribution at the end of step 1 of the analysis, i.e., before the introduction of the pore. As can be seen, except for some edge effects, the free charge density is constant over the surfaces of the membrane, being positive on the extracellular side and negative on the intracellular side.

The lower portion of FIG. 5 shows the charge distribution at the end of step 2. As can be seen, negative free charge has accumulated on the pore's wall at its entrance end on the extracellular side of the membrane and positive free charge has accumulated on the wall at the pore's exit end on the intracellular side. (Note that "entrance" and "exit" are used in the sense of positive charge (positive current) moving inward from the extracellular side of the membrane.) Significantly, these accumulated charges within the interior of the pore have a sign opposite to that of the charges which remain on the adjacent planar surfaces of the membrane.

The negative charges at the entrance to the pore on the extracellular side can be thought of as creating a turning force directing the positive current, which is flowing inward towards the pore along the extracellular surface of the membrane, into the pore. Similarly, the positive charges at the exit to the pore on the intracellular side can be thought of as creating a turning force which turns the current which is flowing in the pore laterally so that it can flow along the intracellular surface of the membrane. Accordingly, as indicated above, these charges are referred to as "current-turning charges."

FIGS. 6-9 show the changes in charge distributions with time. The simplest point to examine is that along the midline of the pore and just outside the pore. This point is identified as the "FIG. 6" point in FIG. 4.

Just prior to the formation of the pore, the extracellular membrane surface at this point and surrounding points carries a free charge density of ~+800 unit charges/$\mu m^2$ for the parameters used in this example. Once the pore opens, this charge and its matching negative charge at the exit end of the pore are no longer held apart by the high resistance membrane and thus can flow towards one another and cancel out. This cancellation occurs essentially at the relaxation time of the medium, which for the conductivity and dielectric constant used in this analysis is 22 ps ($\varepsilon_0/\sigma = (10^{-9}/36\pi$ farads/meter)/(0.4 siemens/meter)=$2.2 \times 10^{-11}$ seconds). An exponential fit ($Ae^{-t/\tau}$) to the time data of FIG. 6 gave a $\tau$ value of 19 ps ($R^2$=0.9994), i.e., of the same order of magnitude as the $\varepsilon_0/\sigma$ ratio.

Figure 7:
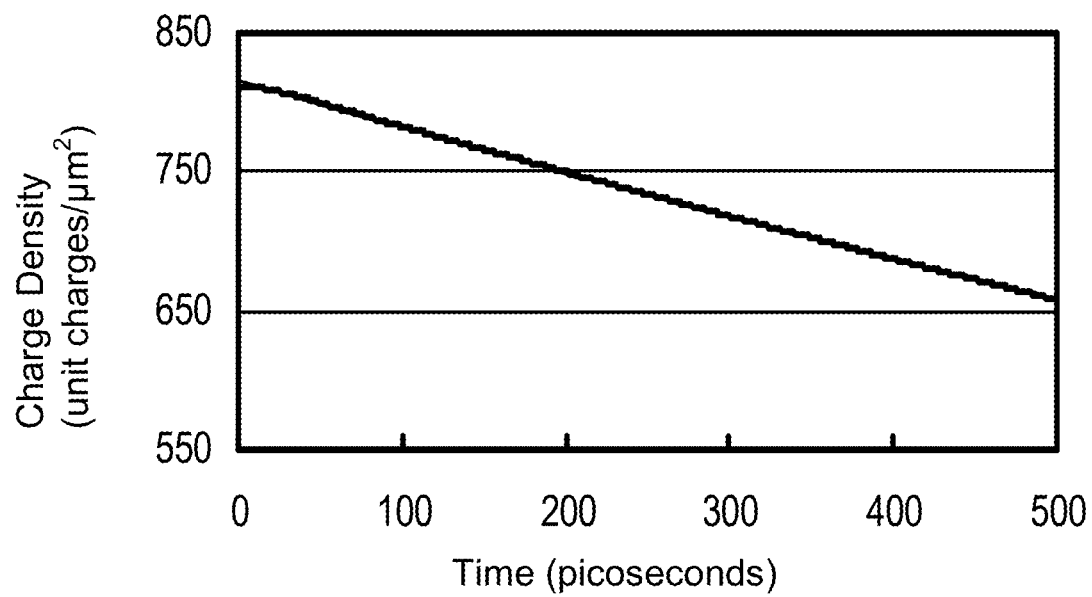
FIG. 7 shows the time course of charge decay at the "FIG. 7" point of FIG. 4. The time constant τ for the decay is 2,320 picoseconds which corresponds to the RC time constant of the overall system.

Another point whose time behavior is easy to understand is that identified as the "FIG. 7" point in FIG. 4. This point is relatively far from the pore and thus, as shown in FIG. 7, its behavior is essentially a decline in magnitude with time following the RC time constant of the overall system. Accordingly, instead of a $\tau$ value of 19 ps as found for FIG. 6, an exponential fit to the time data of FIG. 7 gives a $\tau$ value of 2,320 ps ($R^2$=0.9998), more than 100 times longer. (When comparing the behavior of the free charge densities at the FIG. 6 and FIG. 7 points, note that the horizontal scale of FIG. 7 is ten times greater than that of FIG. 6.)

The "FIG. 8" point in FIG. 4 has a more complex behavior. This point is near to the pore but outside of it on the extracellular surface of the membrane. It undergoes a two phase decrease in its free charge density. The first faster phase involves charge rearrangement so as to produce the charge distribution of the lower panel of FIG. 5 which turns the current into the pore. An exponential fit to the first 100 ps of the time data of FIG. 8 gives a $\tau$ value of 1,065 ps ($R^2$=0.9824), intermediate between the $\tau$ value for the center-of-the pore point of FIG. 6 and that for the remote, extracellular surface point of FIG. 7.

Following this relatively rapid phase, the FIG. 8 point joins the rest of the system and undergoes a decline in charge density in accordance with the system's overall RC time constant. An exponential fit to the 100-500 ps data of FIG. 8 gives a $\tau$ value of 2,500 ps ($R^2$=0.9975), i.e., of the same order of magnitude as the $\tau$ value for the extracellular surface point of FIG. 7.

The "FIG. 9" point of FIG. 4 is the most interesting. This point lies in the region that develops the opposite signed current-turning charges. As a result, its time course is not monotonic. Rather, the charge density versus time plot has a first phase in which the magnitude of the free charge density increases rapidly, followed by a relatively flat phase which transitions into a steady decline in the magnitude of the free charge at the RC time constant of the overall system (an exponential fit to the data points from 400 ps to 500 ps gives a $\tau$ value of 2,480 ps ($R^2$=0.9997)). The current-turning charges thus build up quickly and then decay away along with the rest of the charge in the system.

Because of the symmetry of the system, the time plots of FIGS. 6-9 also apply to the corresponding points on the intracellular side of the membrane but with the opposite sign. The time plots are invariant to a change in the geometric scale of the system; except for FIG. 6, the time constants become longer if the area of the membrane patch is increased while holding the pore dimensions constant, as would be expected.

The changes in transmembrane potential measured at distances remote from the membrane are remarkably mundane and do not reflect the complex changes in charge distribution taking place in the region of the pore. FIG. 10 shows the potential difference as a function of time between the $\Phi_i - \Phi_e$ points of FIG. 4.

As can be seen, even though these points are directly above and below the pore, except for a very slight increase in slope immediately after the pore opens, the difference in potential simply drops in magnitude in accordance with the RC time constant of the overall system (an exponential fit to the data of FIG. 10 gives a ti value of 2,114 ps ($R^2$=0.9957)).

The above calculations, as well as those relating to the pores of Examples 2 and 3, are subject to the standard caveats that macroscopic equations are being used to describe phenomena which are occurring on the Angstrom level. Also, the calculations do not include, for example, the effects of fixed charges, polarization charges, ion concentrations, and asymmetric pore geometries. Nevertheless, as illustrated by these examples, the computer-based computational tools of the invention generate charge distributions not unlike those postulated for the molecules which line the walls of biological pores and thus provide insight into why those charges may be there. Also, the short, pre-steady decay, time constants identified using the computer-based computational tools raise the possibility that high speed ion rearrangements associated with the opening of a pore may be a basis for information processing at rates much faster than those predicted by classical RC time constants.

Example 2

This example illustrates the use of Equations (1)-(2) and (4)-(6) to calculate a charge distribution produced by an active pore.

FIG. 11 shows the system that was analyzed. A square patch of a planar membrane having an area of 140 Å×140 Å, a thickness of 80 Å, and zero conductivity was placed between two 20 Å layers of a biological fluid having a conductivity of 4 siemens/meter (resistivity=25 ohm-cm). The membrane patch was assumed to include a low resistance path at its outer edge (the "perimeter path") having a thickness of 4 Å.

The active pore was a square having 20 Å sides located at the center of the planar membrane. The conductivity of the fluid filling the pore was the same as that of the surrounding media, i.e., 4 siemens/meter. The media were assumed to have different ionic compositions and the pore was assumed to be ion selective so as to generate a Nernst potential of −100 millivolts (intracellular minus extracellular).

The interface between the extracellular and intracellular media (the Nernst surface) was placed at the midplane of the pore and thus Equations (1), (4), and either (5) or (6) were used for all calculation cells having a face at this interface. For all other calculation cells, Equations (1) and (2) were used. Calculation cells having zero conductivity, i.e., those located within the bulk of the membrane (but not those of the perimeter path), were skipped during the iterative process since their q values are zero at all times.

The overall volume was divided into 35×35×30 calculation cells having an edge length (s value) of 4 Å. A time step ($\Delta t$) of 1 picosecond was used in the calculations. The system's 8-fold symmetry was used to reduce computation time. Iterations were continued until the charge distribution stopped changing to at least six significant figures.

The results of the analysis are shown by the topographic plots of FIG. 12 and the midline plots of FIG. 13 for the case of a perimeter path having the same conductivity as that of the media and the pore, i.e., 4 siemens/meter. In particular, FIGS. 12A and 13A show the charge density in unit charges per square micron on the extracellular surface of the membrane, while FIGS. 12B and 13B show the potential distribution in millivolts at that surface. The charge and potential distributions on the intracellular surface have the same configurations, but are the negative of those on the extracellular surface.

As is immediately evident from a comparison of the A panels of these figures with the B panels, the charge distribution (FIGS. 12A and 13A) is substantially more complex and interesting than the potential distribution (FIGS. 12B and 13B). As would be expected, the potential distribution is monotonic, having a maximum value at the center of the pore which declines as one moves towards the perimeter path.

The charge distribution, on the other hand, is anything but monotonic. At the pore, the charge distribution is zero as would be expected since there is neither a conductivity difference nor an active surface at the interface between the medium and the end of the pore. Far from the pore, the charge distribution on the extracellular surface is positive, as could be predicted from the positive potentials of that surface.

However, surrounding the pore is a completely unexpected ring of charge whose sign is opposite to that of the predicted positive charge for an extracellular surface whose potential is positive. That is, one would predict only positive charges on a positive surface, yet in FIGS. 12A and 13A, the charge distribution has a ring surrounding the pore which is negatively charged. Moreover, as shown in FIG. 14, this ring has a substantial width extending out from the pore for this system by approximately the width of the pore.

Although a ring of negative charge is unexpected, once observed, the ring can be understood in terms of the current turning charges discussed above in connection with Example 1. As in Example 1, the current flowing through the pore needs to change direction when it reaches the media which bound the pore. As shown by Rosser (1970), a change in current direction requires an accumulation of charge in the vicinity of the location where the change in direction occurs.

For the case of a passive pore (Example 1), current turning charges of opposite sign are found inside the pore (see FIG. 5). For an active pore, the proximity of the active surface (the Nernst surface) causes the charges within the pore to have the same sign as the local potential, i.e., for the present system, the charges within the pore on the extracellular side of the Nernst surface are positive, while those on the intracellular side of the Nernst surface are negative (data not shown). As a result, for an active pore, the reverse-sign, current-turning charges are not located within the pore but appear in a ring around the mouth of the pore.

The direct association of the ring of reverse-sign charges with the flow of current through the pore is illustrated in FIGS. 15 and 16. FIG. 15 repeats the plot of FIG. 13A (see triangular data points in FIG. 15) and also adds two additional curves obtained under the same conditions, but for smaller perimeter conductivities, i.e., 2 siemens/meter for the square data points and 1 siemens/meter for the circular data points, as compared to 4 siemens/meter for the triangular data points. These reduced conductivities mean that less current is passing through the pore. As shown in FIG. 15, the magnitude and width of the reverse-sign, current-turning charges are reduced as the current through the pore is reduced.

FIG. 16 uses the data of FIG. 15, as well as additional data for perimeter conductivities of 0.5 siemens/meter, 6 siemens/meter, and 8 siemens/meter, to relate the maximum value of the reverse-sign, current-turning charge density to the ratio of the perimeter path conductivity to the pore conductivity. As can be seen in this figure, as the conductivity of the perimeter path decreases, the magnitude of the reverse-sign charges decreases until for a perimeter path having zero conductivity, the reverse-sign charges disappear (data not shown). As the conductivity of the perimeter path increases, the magnitude of the reverse-sign charges increases and then levels off. The leveling off occurs because the current through the pore is a function of the series combination of the resistance of the pore, the resistance of the media between the pore and the perimeter path (including the access resistances to the pore and to the perimeter path), and the resistance of the perimeter path. Once the resistance of the perimeter path becomes sufficiently small, additional reductions in its resistance (additional increases in its relative conductivity) make little difference since the resistance of the system and thus the current through the pore is dominated by the pore and media resistances.

The phenomena reported in this example are significant in view of the numerous studies of biological pores that have associated the regions around the mouths of pores with biological functions, including the binding of charged ligands, which are capable of affecting pore function, to binding sites in these regions. See, for example, Hille (2001). The reverse-sign, current-turning charges discovered using the computer-based computational tools of the invention provide a mechanism for the movement of such charged ligands to and from such binding sites. Prior to the analysis of this example, which was enabled by the computer-based computational tools of this invention, no mechanism of this kind was known in the art.

Example 3

This example illustrates the use of Equations (1) and (2) to calculate a charge distribution associated with a difference in conductivity between the media on the intracellular and extracellular sides of a passive pore. It also illustrates the application of an applied current to a pore.

FIG. 17 shows the system that was analyzed. A square patch of a planar membrane having an area of 140 Å×140 Å, a thickness of 80 Å, and zero conductivity was placed between two 20 Å layers of biological fluid which in the initial analysis had equal conductivities of 0.727 siemens/meter (resistivity=137.5 ohm-cm). The pore was a square having 20 Å sides located at the center of the planar membrane. In the initial analysis, the conductivity of the fluid filling the pore was the same as that of the surrounding media, i.e., 0.727 siemens/meter.

The overall volume was divided into 35×35×30 calculation cells having an edge length (s value) of 4 Å. A time step (Δt) of 1 picosecond was used in the calculations. The system's 8-fold symmetry was used to reduce computation time. Equations (1) and (2) were used for all calculation cells except those having zero conductivity, i.e., those located within the bulk of the membrane, which were skipped during the iterative process since their q values are zero at all times. Iterations were continued until the charge distribution stopped changing to at least six significant figures.

At the beginning of each iteration step, charge was introduced into the calculation cells making up the top plane of the intracellular medium and removed from the calculation cells making up the bottom plane of the extracellular medium. The same amount of charge was introduced (removed) from each of these intracellular (extracellular) calculation cells. The total current ($I_{applied}$) introduced was the same as that removed and was selected so that the transmembrane potential at steady state was on the order of 100 millivolts. In particular, a current of 35 picoamps was found to produce a potential difference between the points at the center of the pore on the intracellular and extracellular surfaces of the membrane of +98 millivolts when the pore and media conductivities were 0.727 siemens/meter. (This voltage difference was substantially the same for the system analyzed below in FIGS. 19 and 20, i.e., +103 millivolts.) The results of the initial analysis using equal conductivities for the bathing media and the pore are shown in FIG. 18 which plots charge density along a midplane at the intracellular and extracellular surfaces of the membrane. As shown in this figure, the charge distributions are symmetric and include relatively flat portions between the location of the pore, where, as expected, the charge density drops to zero, and the edge of the membrane, where, as also expected, the charge density increases rapidly as a result of edge effects. Edge effects of the type shown in FIG. 18 are ubiquitous in systems where a conductor meets a non-conductor and are especially large at corners, including the corners formed by the intersection of a high resistance membrane with a surrounding insulator such as the wall of a micropipette.

FIG. 19 shows the effects on the charge distribution of replacing the media of FIG. 18 with an intracellular medium having a conductivity of 0.4 siemens/meter (resistivity=250 ohm-cm) and an extracellular medium having a conductivity of 4.0 siemens/meter (resistivity=25 ohm-cm). The pore is assumed to be half filled with the intracellular medium and half filled with the extracellular medium, i.e., the conductivity interface (see FIG. 17B) occurs at the midplane of the pore. This combination of conductivities gives the same overall resistance for the pore as that of the initial analysis, i.e., for the initial analysis R=L/(σA)=80 Å/(0.727 siemens/meter×20 Å×20 Å)=2.75 gigaohm, while for the analysis of FIG. 19, R=40 Å/(0.4 siemens/meter×20 Å×20 Å)+40 Å/(4.0 siemens/meter×20 Å×20 Å)=2.50 gigaohm+0.25 gigaohm=2.75 gigaohm.

For ease of comparison, FIG. 19 repeats the charge distribution of FIG. 18 obtained for equal conductivities (see the solid curve) and also shows the changed distribution that results from the unequal conductivities (see the dashed curve). As the dashed curve shows, the unequal conductivities generate a ring of charge that surrounds the pore on the intracellular side of the membrane. This ring is also shown in the topographic plot of FIG. 20.

The ring of charge of FIGS. 19 and 20 is again involved in current turning. For the system of FIG. 18, i.e., the equal conductivity case, the turning charges are found inside the pore (data not shown). Thus, the turning charges for this case are like those of Example 1. For the system of FIGS. 19 and 20, negative charge accumulates at the conductivity interface at the midplane of the pore, as well as along the wall of the pore (data not shown). Such negative charge increases the electric field in the low conductivity medium, i.e., the intracellular medium, as is needed so that the current leaving that medium equals the current entering the high conductivity medium, i.e., the extracellular medium. However, in terms of turning charges, this negative charge is excessive and thus the ring of enhanced, in this case, positive charge develops on the intracellular surface around the mouth of the pore to produce the proper amount of turning of the current into the pore.

It should be noted that the reduced charge densities in the vicinity of the pore on the extracellular side of the membrane shown in FIG. 19 (see the lower branch of the dashed curve) can also be viewed as a charge ring, i.e., a positive charge ring superimposed on the lower branch of the solid curve. Because of the conductivity interface at the midplane of the pore, the charges along the wall of the pore on the extracellular side of the midplane are negative, whereas in FIG. 18 (the equal conductivity case), they are positive (data not shown). The reduction in negative charge density on the extracellular surface of the membrane in the vicinity of the pore compensates for this loss of positive turning charge within the pore and thus achieves the proper turning of current flowing out of the pore and into the surrounding extracellular medium.

As with the charge rings of Example 2, the charge rings of this example were not known in the art prior to the development of the computer-based computational tools of the present invention. As discussed above, these charge rings are of particular value experimentally since the conductivities of media bathing a pore are routinely changed in, for example, patch clamp experiments. Thus, the production of these charge rings is under the control of research scientists performing electrophysiological experiments.

H. Features

Based on the foregoing, the invention includes, but is not limited to, the following features. The features, as well as their various paragraphs and subparagraphs, can be used in any and all combinations.

1. A computer-based method for computing a spatial distribution, a time series, or a spatial distribution and a time series of at least one electrical variable of an electrophysiological system that comprises a biological membrane comprising:

(i) an intracellular side,
(ii) an extracellular side, and
(iii) at least two membrane regions with different electrical properties, said method comprising using a computer to determine a spatial charge distribution for at least a portion of the system using a $1/r^2$ law to express at least some of the system's electrical fields, where the r's represent distances to quantities of charge, said spatial charge distribution being determined without first determining an electrical potential distribution and then differentiating that potential distribution to determine the charge distribution.

2. The method of Feature 1 wherein the at least one electrical variable is an electrical potential difference, an electric field, a current density, a total current, a surface charge density, a total quantity of charge, a capacitance value, a resistance value, or a time constant.

3. The method of Feature 1 wherein the at least two membrane regions comprises a first membrane region having a first conductivity $\sigma_{r1}$ and a second membrane region having a second conductivity $\sigma_{r2}$, where:

$$\sigma_{r1} < \sigma_{r2}.$$

4. The method of Claim 3 wherein the first membrane region constitutes the majority of the membrane and the second membrane region constitutes a conductive path through the membrane.

5. The method of Feature 4 wherein the second membrane region is a pore.

6. The method of Feature 4 wherein the second membrane region contacts at least a portion of the outer perimeter of the first membrane region.

7. The method of Feature 6 wherein the second membrane region contacts the entire outer perimeter of the first membrane region.

8. The method of Feature 1 wherein the at least two membrane regions comprises:
   (i) a non-active membrane region, and
   (ii) an active membrane region,
the active region differing from the non-active region in that only conservative fields act at the non-active region while both conservative and non-conservative fields act at the active region.

9. The method of Feature 8 wherein the active membrane region is a pore.

10. The method of Feature 8 wherein the active membrane region contacts at least a portion of the outer perimeter of the non-active membrane region.

11. The method of Feature 8 wherein the membrane is selective for an ion at the active membrane region and the non-conservative field represents a concentration difference for that ion between media on the intracellular and extracellular sides of the membrane.

12. The method of Feature 8 wherein:
   (a) a plurality of cubic calculation cells are used to determine said spatial charge distribution; and
   (b) quantities of charge entering/leaving at least some of the calculation cells associated with the active membrane region are determined using equations of the form:

$$\Delta q = -\sigma(E_n + E'_n)s^2 \Delta t;$$

where $\Delta q$ is the quantity of charge entering into a face of a calculation cell during a time step $\Delta t$, s is the length of an edge of the face, $\sigma$ is the smaller of the conductivities on the inside and outside of the face, and $E_n$ and $E'_n$ are fields acting in the direction of the face's outward normal, $E_n$ being the net outward normal electric field at the center of the face determined using the $1/r^2$ law, and $E'_n$ being the non-conservative field which acts at the face.

13. The method of Feature 12 wherein:
   (i) the membrane is selective for an ion at the active membrane region;
   (ii) the non-conservative field represents a concentration difference for that ion between media on the intracellular and extracellular sides of the membrane;
   (iii) the concentration difference has a Nernst potential $V_{Nernst}$ between the intracellular and extracellular sides of the membrane;
   (iv) $E'_n$ is determined using an equation of the form:

$$E'_n = -V_{Nernst}/s,$$

if the face's outward normal points from the intracellular side of the face towards the extracellular side of the face; and
   (v) $E'_n$ is determined using an equation of the form:

$$E'_n = +V_{Nernst}/s$$

if the face's outward normal points from the extracellular side of the face towards the intracellular side of the face.

14. The method of Feature 1 wherein:
   (i) the system comprises a first zone at which quantities of charge are introduced into the system and a second zone at which quantities of charge are removed from the system; and
   (ii) the rate at which quantities of charge are introduced at the first zone equals the rate at which quantities of charge are removed at the second zone.

15. The method of Feature 1 wherein the system comprises a first volume on the extracellular side of the membrane having a conductivity $\sigma_{ext}$ and a second volume on the intracellular side of the membrane having a conductivity $\sigma_{int}$, where:

$$\sigma_{ext} \neq \sigma_{int}.$$

16. A computer-based method for computing a spatial charge distribution for at least a portion of an electrophysiological system that comprises a biological membrane, said method comprising using a computer to:
   (a) represent at least a portion of the system by a plurality of cubic calculation cells; and
   (b) calculate a quantity of charge entering/leaving at least one calculation cell using an equation of the form:

$$\Delta q = -\sigma(E_n + E'_n)s^2 \Delta t;$$

where $\Delta q$ is the quantity of charge entering into a face of the calculation cell during a time step $\Delta t$, s is the length of an edge of the face, $\sigma$ is the smaller of the conductivities on the inside and outside of the face, and $E_n$ and $E'_n$ are fields acting in the direction of the face's outward normal, $E_n$ being the net outward normal electric field at the center of the face produced by the spatial charge distribution at the beginning of the time step, and $E'_n$ being a non-conservative field which acts at the face.

17. A computer-based method for computing a spatial charge distribution for at least a portion of an electrophysiological system that comprises a biological membrane having an intracellular side and an extracellular side, said method comprising using a computer to:
   (a) represent said portion of the system by a plurality of cubic calculation cells, each calculation cell having six faces and edges of length s;
   (b) represent a non-conservative field $E'_n$ at a face of at least one calculation cell by an equation of the form:

$$E'_n = -V_{Nernst}/s,$$

said face having an outward normal that points from the intracellular side of the face towards the extracellular side of the face; and
   (c) represent a non-conservative field $E'_n$ at a face of at least one calculation cell by an equation of the form:

$$E'_n = +V_{Nernst}/s$$

said face having an outward normal that points from the extracellular side of the face towards the intracellular side of the face;

where $V_{Nernst}$ is a Nernst potential between the intracellular and extracellular sides of the membrane.

18. A computer-based method for computing a spatial charge distribution for a portion of an electrophysiological system that comprises a biological membrane comprising:
  (i) an inner region,
  (ii) a perimeter region which contacts at least a portion of the outer perimeter of the inner region, and
  (iii) an outer region located outboard of the perimeter region, said method comprising using an electrical property of at least a portion of the perimeter region to represent at least a portion of the outer region and thereby avoid the need to explicitly calculate a spatial charge distribution for said at least a portion of the outer region.

19. A computer-based method for computing a spatial charge distribution for at least a portion of an electrophysiological system that comprises a biological membrane, said method comprising using a computer to:
  (a) represent at least a portion of the system by a plurality of cubic calculation cells; and
  (b) calculate a quantity of charge entering/leaving at least one calculation cell using an equation having a form selected from the group consisting of:

$$\Delta q = -E_n s^3 \Delta t / R_m \text{ and } \Delta q = -(E_n + E'_n) s^3 \Delta t / R_m;$$

where $\Delta q$ is the quantity of charge entering into a face of the calculation cell during a time step $\Delta t$, s is the length of an edge of the face, $R_m$ is the specific resistance of a portion of the biological membrane located at the face, and $E_n$ and $E'_n$ are fields acting in the direction of the face's outward normal, $E_n$ being the net outward normal electric field at the center of the face produced by the spatial charge distribution at the beginning of the time step, and $E'_n$ being a non-conservative field which acts at the face.

20. A computer-based method for computing a spatial charge distribution associated with a biological membrane comprising using a computer to:
  (a) represent the membrane as being located between two volumes of conductive media each volume being bounded by non-conductive walls except for the portion of the volume bounded by the membrane; and
  (b) determine a spatial charge distribution on at least a portion of the surface of the membrane using a $1/r^2$ law to express electrical fields, where the r's represent distances to quantities of charge.

21. The method of Feature 20 wherein the membrane is homogeneous.

22. The method of Feature 20 wherein the membrane is inhomogeneous.

23. The method of Feature 22 wherein the membrane comprises a pore.

24. The method of Feature 23 wherein the pore is an active pore.

25. The method of Feature 22 wherein the membrane comprises a low resistance perimeter.

26. The method of Feature 20 wherein the volumes are homogeneous.

27. The method of Feature 26 wherein at least one of the volumes is inhomogeneous.

28. The method of Feature 27 wherein the at least one inhomogeneous volume comprises at least one additional membrane.

29. The method of Feature 28 wherein the at least one additional membrane is homogeneous.

30. The method of Feature 28 wherein the at least one additional membrane is inhomogeneous.

31. The method of Feature 30 wherein the at least one inhomogeneous additional membrane comprises a pore.

32. The method of Feature 31 wherein the pore is an active pore.

33. The method of Feature 30 wherein the at least one inhomogeneous additional membrane comprises a low resistance perimeter.

34. The method of Feature 27 wherein the at least one inhomogeneous volume comprises at least one current source.

35. A computer-based method for computing a spatial charge distribution for at least a portion of an electrophysiological system that comprises a biological membrane having an intracellular side and an extracellular side, said method comprising:
  (I) inputting data to a computer regarding (i) the structure and dimensions of the portion of the electrophysiological system, (ii) at least one electrical property of the portion of the electrophysiological system, and (iii) the value $V_{Nernst}$ of at least one Nernst potential between the intracellular and extracellular sides of the biological membrane;
  (II) using the computer to:
    (a) represent said portion of the electrophysiological system by a plurality of cubic calculation cells, each calculation cell having six faces and edges of length s;
    (b) represent a non-conservative field $E'_n$ at a face of at least one calculation cell by an equation of the form:

$$E'_n = -V_{Nernst}/s,$$

said face having an outward normal that points from the intracellular side of the face towards the extracellular side of the face;

(c) represent a non-conservative field $E'_n$ at a face of at least one calculation cell by an equation of the form:

$$E'_n = +V_{Nernst}/s$$

said face having an outward normal that points from the extracellular side of the face towards the intracellular side of the face; and
    (d) determine the spatial charge distribution for said portion of the electrophysiological system using (i) the plurality of cubic calculation cells, (ii) the representations of the non-conservative field, and (iii) a $1/r^2$ law to express at least some of the electrophysiological system's electrical fields, where the r's represent distances to quantities of charge, said spatial charge distribution being determined without first determining an electrical potential distribution and then differentiating that potential distribution to determine the charge distribution; and (III) displaying at least a part of the spatial charge distribution for said portion of the electrophysiological system determined in step (II)(d).

36. Apparatus comprising a computer which has been programmed to perform the method of Feature 1, 16, 17, 18, 19, 20, or 35.

37. An article of manufacture comprising a computer readable storage medium having computer readable code embodied therein for performing the method of Feature 1, 16, 17, 18, 19, 20, or 35.

As discussed above, experimental measurements provide the electrical, chemical, structural, and dimensional properties of the electrophysiological systems and/or biological membranes referred to in these features. The various computations referred to in the features transform the data provided by those experimental measurements into forms, e.g., spatial charge distributions, which are displayed and/or used to interpret the underlying physiological phenomena which generated the experimental data. The transformed data is also used in the design of further experiments.

A variety of modifications that do not depart from the scope and spirit of the invention will be evident to persons of ordinary skill in the art from the foregoing disclosure. The following claims are intended to cover the specific embodiments set forth herein as well as such modifications, variations, and equivalents.

REFERENCES

Allen, R., Hansen, J.-P., and Melchionna, S., "Electrostatic potential inside ionic solutions confined by dielectrics: a variational approach," *Phys. Chem. Chem. Phys.*, vol. 3, pp. 4177-4186, 2001.

Carnevale, T. and Hines, M., *The NEURON Book*, Cambridge, UK, Cambridge University Press, 2005.

Chabay, R. and Sherwood, B., *Matter and Interactions*, vol. II, New York, N.Y., John Wiley & Sons, 2002.

Heald, M. A., "Electric fields and charges in elementary circuits," *Am. J. Phys.*, vol. 52, no. 6, pp. 522-526, June 1984.

Hermann, L., "Beitrage zur Physiologie und Physik des Nerven," *Pflugers Arch.*, vol. 109, pp 95-144, 1905.

Hille, B., *Ion Channels of Excitable Membranes*, 3rd ed., Sunderland, Mass.: Sinauer Associates, 2001.

Huang, C.-J., Harootunian, A., Maher, M. P., Quan, C., Raj, C. D., McCormack, K., Numann, R., Negulescu, P. A., and Gonzilez, J. E., "Characterization of voltage-gated sodium-channel blockers by electrical stimulation and fluorescence detection of membrane potential," *Nature Biotechnology*, vol. 24, no. 4, pp. 439-446, April 2006.

Islas, L. D. and Sigworth, F. J., "Electrostatics and the gating pore of Shaker potassium channels," *J. Gen. Physiol.*, vol. 117, pp. 69-89, January 2001.

Jackson, J. D., "Surface charges on circuit wires and resistors play three roles," *Am. J. Phys.*, vol. 64, no. 7, pp. 855-870, July 1996.

Jefimenko, O. D., *Electricity and Magnetism*, 2nd ed., Star City, W. Va.: Electret Scientific, 1989.

Koch, C., and Segev, I. (eds.), *Methods in Neuronal Modeling: From Ions to Networks*, 2nd edition, Cambridge, Mass., The MIT Press, 1998.

Plonsey, R., *Bioelectric Phenomena*, McGraw-Hill Series in Bioengineering, New York, N.Y., McGraw-Hill, 1969.

Plonsey, R. and Barr, R. C., *Bioelectricity A Quantitative Approach*, 2nd ed., New York, N.Y.: Kluwer Academic/Plenum Publishers, 2000, Chapter 4.

Preyer, N. W., "Surface charges and fields of simple circuits," *Am. J. Phys.*, vol. 68, no. 11, pp. 1002-1004, November 2000.

Preyer, N. W., "Transient behavior of simple RC circuits," *Am. J. Phys.*, vol. 70, no. 12, pp. 1187-1193, December 2002.

Rosser, W. G. V., "Magnitudes of surface charge distributions associated with electric current flow," *Am. J. Phys.*, vol. 38, no. 2, pp. 265-266, February 1970.

What is claimed is:

1. A computer-implemented method for modeling at least a portion of an electrophysiological system comprising:
   (A) generating, in a computer, a model of the at least a portion of an electrophysiological system, the model comprising: (i) an interface between two volumes that have different conductivities, (ii) a first zone for introducing quantities of charge into the system, and (iii) a second zone for removing quantities of charge from the system, and
   (B) computing and displaying, using a computer, a charge distribution for at least a portion of the interface between the two volumes at at least two points in time, where computing the charge distribution comprises:
      (i) directly calculating quantities of charge located along the interface between the two volumes without first computing an electric potential distribution and thereafter taking a derivative of that electric potential distribution to determine the charge distribution,
      (ii) introducing a quantity of charge into at least one calculation cell in the first zone and removing a quantity of charge from at least one calculation cell in the second zone, and
      (iii) using said introducing of a quantity of charge into at least one calculation cell in the first zone and said removing of a quantity of charge from at least one calculation cell in the second zone as part of said directly calculating quantities of charge located along the interface between the two volumes.

2. The computer-implemented method of claim 1 wherein the quantity of charge introduced into the at least one calculation cell in the first zone equals the quantity of charge removed from the at least one calculation cell in the second zone.

3. The computer-implemented method of claim 1 further comprising using conservative and non-conservative fields as a part of said directly calculating quantities of charge located along the interface between the two volumes.

4. The computer-implemented method of claim 1 wherein the interface between two volumes having different conductivities is an interface between a biological medium and a biological membrane.

5. The computer-implemented method of claim 1 wherein the interface between two volumes having different conductivities is an interface between a biological medium and a non-conductor.

6. The computer-implemented method of claim 1 wherein the interface between two volumes having different conductivities is an interface between an intracellular biological medium and an extracellular biological medium.

7. The computer-implemented method of claim 1 wherein said at least a portion of an electrophysiological system is a portion of a patch clamp system.

8. A computer-implemented method for modeling at least a portion of an electrophysiological system comprising:
   (A) generating, in a computer, a model of the at least a portion of an electrophysiological system, the model comprising: (i) an interface between two volumes that have different conductivities, (ii) a first zone for introducing quantities of charge into the system, and (iii) a second zone for removing quantities of charge from the system, and
   (B) computing and displaying, using a computer, a charge distribution for at least a portion of the interface between the two volumes, where computing the charge distribution comprises:
      (i) directly calculating quantities of charge located along the interface between the two volumes without first computing an electric potential distribution and thereafter taking a derivative of that electric potential distribution to determine the charge distribution, (ii) introducing a quantity of charge into at least one calculation cell in the first zone and removing a quantity of charge from at least one calculation cell in the second zone, and (iii) using said introducing of a quantity of charge into at least one calculation cell in the first zone and said removing of a quantity of charge from at least one calculation cell in the second zone as part of said directly calculating quantities of charge located along the interface between the two volumes.

9. The computer-implemented method of claim 8 wherein the quantity of charge introduced into the at least one calculation cell in the first zone equals the quantity of charge removed from the at least one calculation cell in the second zone.

10. The computer-implemented method of claim 8 wherein the interface between two volumes having different conductivities is an interface between a biological medium and a biological membrane.

11. The computer-implemented method of claim 8 wherein the interface between two volumes having different conductivities is an interface between a biological medium and a non-conductor.

12. The computer-implemented method of claim 8 wherein the interface between two volumes having different conductivities is an interface between an intracellular biological medium and an extracellular biological medium.

13. The computer-implemented method of claim 8 wherein said at least a portion of an electrophysiological system is a portion of a patch clamp system.

14. The computer-implemented method of claim 8 wherein said introducing and removing charge is used to model cell stimulation.

15. A computer-implemented method for modeling at least a portion of an electrophysiological system comprising:

(A) generating, in a computer, a model of the at least a portion of an electrophysiological system, the model comprising: (i) an interface between two volumes that have different conductivities, (ii) a first zone for introducing quantities of charge into the system, and (iii) a second zone for removing quantities of charge from the system, and (B) computing and displaying, using a computer, a charge distribution for at least a portion of the interface between the two volumes, where computing the charge distribution comprises:

(i) directly calculating quantities of charge located along the interface between the two volumes without first computing an electric potential distribution and thereafter taking a derivative of that electric potential distribution to determine the charge distribution, (ii) introducing a quantity of charge into at least one calculation cell in the first zone and removing a quantity of charge from at least one calculation cell in the second zone, (iii) using said introducing of a quantity of charge into at least one calculation cell in the first zone and said removing of a quantity of charge from at least one calculation cell in the second zone as part of said directly calculating quantities of charge located along the interface between the two volumes, and (iv) using conservative and non-conservative fields as a part of said directly calculating quantities of charge located along the interface between the two volumes.

16. The computer-implemented method of claim 15 wherein the interface between two volumes having different conductivities is an interface between a biological medium and a biological membrane.

17. The computer-implemented method of claim 15 wherein the interface between two volumes having different conductivities is an interface between a biological medium and a non-conductor.

18. The computer-implemented method of claim 15 wherein the interface between two volumes having different conductivities is an interface between an intracellular biological medium and an extracellular biological medium.

19. The computer-implemented method of claim 15 wherein said at least a portion of an electrophysiological system is a portion of a patch clamp system.

20. The computer-implemented method of claim 15 wherein the quantity of charge introduced into the at least one calculation cell in the first zone equals the quantity of charge removed from the at least one calculation cell in the second zone.

* * * * *